(12) United States Patent
Wu

(10) Patent No.: US 11,666,520 B2
(45) Date of Patent: *Jun. 6, 2023

(54) HAIR GROWTH COMPOSITION AND METHOD

(71) Applicant: Johnson & Johnson Consumer Inc., Skillman, NJ (US)

(72) Inventor: Jeffrey M. Wu, Princeton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 69 days.

This patent is subject to a terminal disclaimer.

(21) Appl. No.: 15/387,637

(22) Filed: Dec. 21, 2016

(65) Prior Publication Data

US 2017/0181949 A1 Jun. 29, 2017

Related U.S. Application Data

(60) Provisional application No. 62/271,405, filed on Dec. 28, 2015.

(51) Int. Cl.
| | | |
|---|---|---|
| *A61K 8/49* | (2006.01) | |
| *A61K 31/506* | (2006.01) | |
| *A61K 47/14* | (2017.01) | |
| *A61K 9/00* | (2006.01) | |
| *A61K 47/38* | (2006.01) | |
| *A61K 8/14* | (2006.01) | |
| *A61K 8/34* | (2006.01) | |
| *A61K 8/365* | (2006.01) | |
| *A61K 8/37* | (2006.01) | |
| *A61K 8/39* | (2006.01) | |
| *A61K 8/73* | (2006.01) | |
| *A61Q 7/00* | (2006.01) | |
| *A61K 8/362* | (2006.01) | |
| *A61K 8/86* | (2006.01) | |

(52) U.S. Cl.
CPC .............. *A61K 8/4953* (2013.01); *A61K 8/14* (2013.01); *A61K 8/34* (2013.01); *A61K 8/345* (2013.01); *A61K 8/347* (2013.01); *A61K 8/362* (2013.01); *A61K 8/365* (2013.01); *A61K 8/37* (2013.01); *A61K 8/39* (2013.01); *A61K 8/731* (2013.01); *A61K 8/86* (2013.01); *A61K 9/0014* (2013.01); *A61K 31/506* (2013.01); *A61K 47/14* (2013.01); *A61K 47/38* (2013.01); *A61Q 7/00* (2013.01); *A61K 2800/262* (2013.01); *A61K 2800/48* (2013.01); *A61K 2800/49* (2013.01); *A61K 2800/52* (2013.01); *A61K 2800/594* (2013.01)

(58) Field of Classification Search
CPC .......... A61K 8/4953; A61K 8/14; A61K 8/34; A61K 8/345; A61K 8/347; A61K 8/362; A61K 8/365; A61K 8/37; A61K 8/39; A61K 8/731; A61K 8/86; A61K 9/0014; A61K 31/506; A61K 47/14; A61K 47/38; A61K 2800/262; A61K 2800/48; A61K 2800/49; A61K 2800/52; A61K 2800/594; A61Q 7/00

See application file for complete search history.

(56) References Cited

U.S. PATENT DOCUMENTS

| | | | |
|---|---|---|---|
| 4,874,794 A | 10/1989 | Adachi et al. | |
| 4,897,269 A | 1/1990 | Mezei | |
| 4,987,269 A * | 1/1991 | Petri | C08G 64/10 528/196 |
| 5,133,967 A | 7/1992 | Smith | |
| 5,472,689 A | 12/1995 | Ito | |
| 5,559,092 A | 9/1996 | Gibson | |
| 5,658,956 A | 8/1997 | Martin et al. | |
| 5,747,016 A | 5/1998 | Yui et al. | |
| 5,834,014 A | 11/1998 | Weiner et al. | |
| 5,972,358 A * | 10/1999 | Jampani | A61K 8/37 424/401 |
| 6,051,602 A | 4/2000 | Bissett | |
| 6,284,234 B1 | 9/2001 | Niemiec et al. | |
| 6,419,913 B1 | 7/2002 | Niemiec et al. | |
| 6,803,047 B1 | 10/2004 | Dupuis | |
| 6,946,120 B2 | 9/2005 | Wai-Chiu So et al. | |
| 9,675,537 B2 * | 6/2017 | Wu | A61K 47/12 |
| 9,956,156 B2 * | 5/2018 | Wu | A61K 47/14 |
| 10,561,593 B2 * | 2/2020 | Wu | A61K 8/362 |
| 10,925,824 B2 * | 2/2021 | Wu | A61K 8/37 |
| 11,000,466 B2 * | 5/2021 | Wu | A61K 8/345 |
| 11,039,996 B2 * | 6/2021 | Wu | A61K 8/14 |

(Continued)

FOREIGN PATENT DOCUMENTS

| | | |
|---|---|---|
| CA | 2636392 A1 | 12/2008 |
| DE | 4402527 A1 | 8/1995 |

(Continued)

OTHER PUBLICATIONS

International Search Report—dated Mar. 14, 2017 (PCT/US2016/068185).

(Continued)

*Primary Examiner* — Jeffrey S Lundgren
*Assistant Examiner* — William Y Lee
(74) *Attorney, Agent, or Firm* — Darryl C. Little

(57) ABSTRACT

The present invention relates to compositions for and methods of retarding hair loss or facilitating hair growth comprising a hair growth active, a mixture of $C_{12}$-$C_{15}$ alkyl lactates and a viscosity modifying agent comprising at least one cellulose and/or a cellulose derivative. Clear compositions are also disclosed.

18 Claims, 2 Drawing Sheets

(56) References Cited

U.S. PATENT DOCUMENTS

| | | | |
|---|---|---|---|
| 11,185,487 B2* | 11/2021 | Wu | A61K 8/4953 |
| 2002/0006418 A1 | 1/2002 | Kung et al. | |
| 2002/0037914 A1 | 3/2002 | Delong et al. | |
| 2002/0172693 A1* | 11/2002 | DeLong | A61K 8/365 |
| | | | 424/400 |
| 2004/0142853 A1 | 7/2004 | Patt | |
| 2005/0244509 A1 | 11/2005 | Tsao | |
| 2007/0098663 A1 | 5/2007 | Gupta | |
| 2008/0145331 A1 | 6/2008 | Bruning et al. | |
| 2009/0258850 A1 | 10/2009 | Frincke | |
| 2010/0111878 A1 | 5/2010 | Maor et al. | |
| 2012/0028916 A1 | 2/2012 | Fournial et al. | |
| 2013/0149271 A1 | 6/2013 | Van Gogh | |
| 2017/0181950 A1 | 6/2017 | Wu | |

FOREIGN PATENT DOCUMENTS

| | | |
|---|---|---|
| EP | 0517371 A2 | 12/1992 |
| GB | 2507639 A | 7/2014 |
| JP | H08176068 A | 7/1996 |
| JP | H10218736 A | 8/1998 |
| JP | H1192378 A | 4/1999 |
| KR | 9406529 B1 | 7/1994 |
| KR | 2008-0038710 A | 5/2008 |
| RU | 2287330 C2 | 11/2006 |
| RU | 2452466 C2 | 6/2012 |
| WO | WO 2014/017573 A1 | 1/2014 |
| WO | WO 2015101668 A1 | 7/2015 |
| WO | WO 2016/003970 A1 | 1/2016 |

OTHER PUBLICATIONS

Balakrishnan, P., et al., "Formulation and in vitro assessment of minoxidil niosomes for enhanced skin delivery", Int'l. Journal of Pharmaceutics, Elsevier, Amsterdam, NL, vol. 377, No. 1-2, Jul. 30, 2009, pp. 1-8 (XP026281914).

Moghassemi, Saeid, et al., "Nano-niosomes as nanoscale drug delivery systems: An illustrated review", Journal of Controlled Release, vol. 185, Apr. 18, 2014, pp. 22-36, (XP028854111).

Walker, C.V., et al., "Rheological synergism between ionic and non ionic cellulose gums", Int'l. Journal of Pharmaceutics, Elsevier, Amsterdam, NL., vol. 11, No. 4, Aug. 1, 1982, pp. 309-322, (XP023844684).

Alvarez-Lorenzo, C., et al., "Influence of polymer structure on the rheological behavior of hydroxypropylmethlcellulose-sodium carboxymethylcellulose dispersions", Colloid & Polymer Science, Springer Verlag, Heidelberg, DE., vol. 279, No. 11, Jan. 1, 2001, pp. 1045-1057. (XP002331111).

Sovilj, et al., "Interaction and phase separation in the system HPMC/NaCMC/SDS", Colloids and Surfaces A: Physiochemical and Engineering Aspects, Elsevier, Amsterdam, NL., vol. 298, No. 1-2, Mar. 19, 2007, pp. 94-98. (XP005932974).

Drug Stability, Principles and Practices, Third Edition, Jens T. Cartensen and Chris T. Rhodes, published by Marcel Dekker.

Adv. Drug Deliv. Rev., Penetration Enhancers, Williams AC1, Barry BW, 56(5): 603-18, Mar. 27, 2004.

Journal of Dermatological Science, Miyamoto I., Hamada K., vol. 10, No. 1, pp. 99-99(1), Jul. 1995.

Guide for the Care and Use of Laboratory Animals, NIH Publication No. 85-23.

Smith, et al.: Percutaneous Penetration Enhancers; Taylor & Francis, Boca Raton, London, New York (2006).

Aqualon, Blanose and Bondwell carboxymethylcellulose (CMC): retrieved from internet: http://ww.ashland.com/industries/packaging-printing-and-graphics/paper-and-coatings/aqualon-carboxymethylcellulose. Retrieved Feb. 9, 2018.

Viscosity chart: retrieved from internet: http://www.dixonvalve.com/sites/default/files/product/files/brochures-literature/viscosity%20chart_0.pdf. Retrieved Feb. 9, 2018.

Aqualon: retrieved from internet: http://www.acedemia.edu/20238791/Aqualon_Product_Literature_AQUALON_Sodium_Carboxymethylcellulose_-_Physical_and_Chemical_Properties_PDF_643_KB. Retrieved Feb. 9, 2018.

Liposome: classification, preparation, and applicatins: retrieved from internet: https://www.ncbi.nlm.nih.gov/pmc/articles/PMC3599573/. Retrieved Feb. 9, 2018.

Reddy, et al., "Preparation and Evaluation of Minoxidil Gels for Topical Application in Alopecia," Indian Journal of Pharmaceutical Sciences, 2006, pp. 432-436 (2006).

Glyceryl laurate—Pubchem (retrieved from online website: https://pubchem.ncbi.nlm.nih.gov/Monolaurin. Sep. 12, 2018 (Year: 2018).

Glyceryl myristate—Pubchem (retrieved from online website: https://pubchem.ncbi.nlm.nih.gov/Monomyristin. Sep. 12, 2018 (Year: 2018).

Aldhalimi, M. A. et al. "Promotive effect of topical ketoconazole, minoxidil, and minoxidil with tretinoin on hair growth in male mice" Hindawi Publishing Corporation ISRN Pharmacology vol. 2014, pp. 1-5; article id 575423, http://dx.doi.org/10.1155/2014/575423.

Sakr, et al., "Preparation and evaluation of a multimodal minoxidil microemulsion versus minoxidil alone in the treatment of androgenic alopecia of mixed etiology: a pilot study." Drug Design, Development and Therapy, 2013:7, pp. 413-423, http://dx.doi.org/10.2147/dddt.s43481.

Rossi, et al., "Minoxidil use in dermatology, side effects and recent patent", Recent Patent on inflammation & Allergy Drug Discovery 2012, vol. 6, No. 2, pp. 130-136.

Richard B. Silverman and Mark W. Holladay, The Organic Chemistry of Drug Design and Drug Action (Third Edition), 2014, Prodrugs and Drug Delivery Systems, Drug Development Research 75, Wiley Periodicals, Inc., pp. 471-472.

Final Report on the Safety Assessment of Cetyl lactate and Myristyl lactate, Cosmetic Ingredient Review, Feb. 4, 2009; pp. 97-107. https://journals.sagepub.com/doi/pdf/10.3109/10915818209013150.

Kaiho, F., et al., Enhancing effect of cetyl lactate on the percutaneous absorption of indomethacin in rats; Chemical and Pharmaceutical Bulletin, 1989, N. 37, vol. 4, pp. 1114-1116.

* cited by examiner

HAIR GROWTH COMPOSITION AND METHOD

FIELD OF THE INVENTION

The present invention relates to compositions for and methods of retarding hair loss or facilitating hair growth comprising a hair growth active, a mixture of $C_{12}$-$C_{15}$ alkyl lactates and a viscosity modifying agent comprising at least one cellulose and/or a cellulose derivative. Clear compositions are also disclosed.

BACKGROUND OF THE INVENTION

Alopecia, or hair loss, in its various forms is an ongoing problem afflicting mankind and animals. Men, woman and children can all suffer from alopecia, which can be result of one, or a combination of, factors including genetic factors, hormonal factors, surgery, trauma, chemotherapy, aging, certain drug side effects and stress. The universality of the occurrence of alopecia has led to continuing efforts throughout history to discover compositions for stimulating hair growth and preventing hair loss.

A number of "natural" remedies for alopecia based solely on herbs and plant extracts have been proposed. However, such compounds have proven clinically to have very little if any effect.

Accordingly, an aspect of the present invention is to provide a method for reducing hair loss and facilitate hair growth and/or providing a thicker, denser or richer hair coat.

Another aspect of the present disclosure is concerned with methods of using compositions comprising at least one hair growth stimulator, and at least one $C_5$-$C_{24}$ alcohol ester of a carboxylic acid.

Another aspect of the present invention is improving the temperature stability of solution or gel compositions containing from about 0.1% to about 20% by weight of a hair growth or hair regrowth compound (such as minoxidil or pharmaceutically acceptable addition salts thereof); from about 0.5% to about 10% by weight of an oil phase or oily compound; from about 0% to about 60% of a dihydric alcohol (such as propylene glycol); and from about 0 to about 65% by weight of a $C_2$-$C_4$ alcohol (such as ethanol).

Another aspect of the present invention is providing clear (or reduced turbidity or cloudiness) solution or gel compositions of pH less than 5 containing from about 0.1% to about 20% by weight of a hair growth or hair regrowth compound (such as minoxidil or pharmaceutically acceptable addition salts thereof); from about 0.5% to about 10% by weight of an oil phase or oily compound; from about 0% to about 60% of a dihydric alcohol (such as propylene glycol); and from about 0 to about 65% by weight of a $C_2$-$C_4$ alcohol (such as ethanol).

Another aspect of the present disclosure is concerned with using the disclosed compositions to accelerate the onset of the anagen phase of hair growth in a mammal.

A still further aspect of the present disclosure is concerned with using the disclosed compositions to increase the rate at which terminal hair appears on the skin of a mammal.

Another aspect of the present invention is to provide a method of reducing or preventing hair thinning and hair loss.

Still other aspects and advantages of the present disclosure will become readily apparent to those skilled in the art from the following detailed description, wherein it is shown and described only in the preferred embodiments, simply by way of illustration of the best mode. As will be realized, the disclosure is capable of other and different embodiments, and its several details are capable of modifications in various obvious respects, without departing from the spirit of the disclosure. Accordingly, the description is to be regarded as illustrative in nature and not as restricted.

SUMMARY OF THE INVENTION

Figure 1:
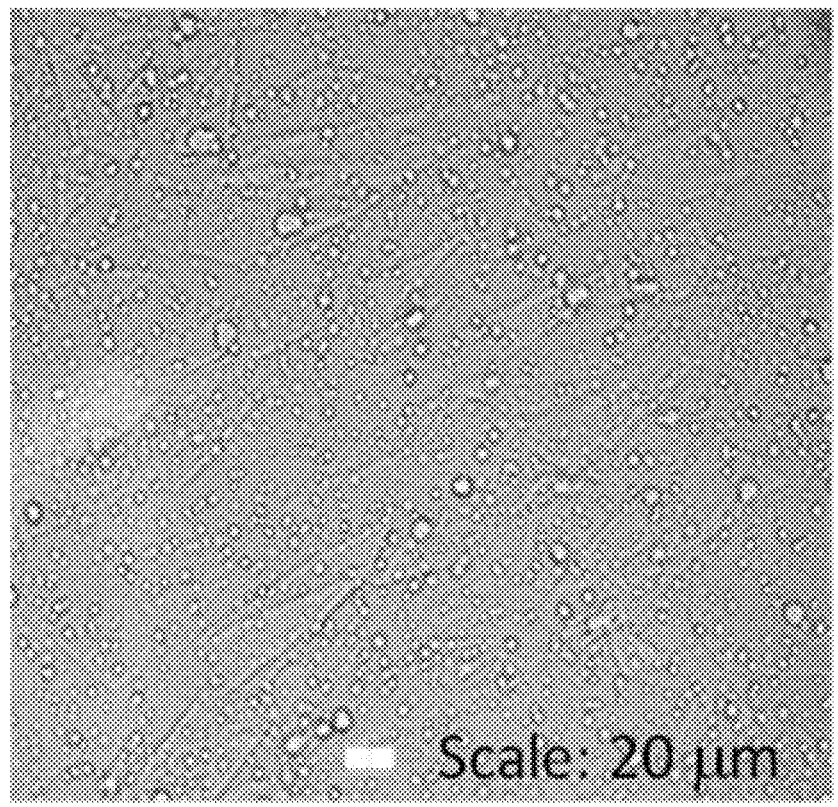
FIG. 1 is picture of a microscopic field of view as obtained using a Olympus BX51 Microscope as described below.

In certain embodiments, the present invention relates to a composition comprising:
a. liquid vesicles comprise:
  i. one or more of a hair growth or hair regrowth compound represented by formulas I or II:

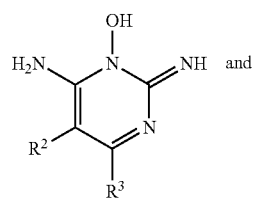

Formula I

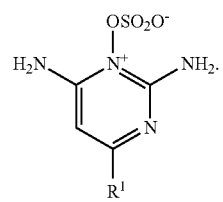

Formula II and mixtures thereof, wherein $R^1$ is hydrogen or —$N(R^3)(R^4)$. Each $R^3$ and $R^4$ individually is selected from the group consisting of hydrogen, lower alkyl, lower alkenyl, lower aralkyl, and lower cycloalkyl, and taken together $R^3$ and $R^4$ may be a heterocyclic moiety selected from the group consisting of aziridinyl, azetidinyl, pyrrolidinyl, piperidino, hexahydroazepinyl, heptamethylenimino, octamethylenimino, morpholino, and 4-lower-alkylpiperazinyl, each of said heterocyclic moieties having attached as substituents on the carbon atoms 0 to 3 lower alkyl groups, hydroxy or alkoxy, and wherein $R^2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl; tautomers thereof and pharmacologically acceptable acid addition salts thereof; and
  ii. a mixture of $C_{12}$-$C_{15}$ alkyl lactates;
b. a viscosity modifying agent comprising at least one cellulose or derivative thereof; and
c. a pharmaceutically acceptable liquid carrier comprising, one or more solubilizer(s), one or more solubilizing acid(s) or mixtures thereof;

wherein the liquid vesicles are suspended within the pharmaceutically acceptable liquid carrier.

In certain embodiments, the present invention relates to a method of growing hair in a subject in need of such treatment, comprising topically applying the above described composition to the subject on an area where hair growth is desired

DETAILED DESCRIPTION OF THE INVENTION

The compositions of the present invention can comprise, consist of, or consist essentially of the essential elements, steps and limitations of the invention described herein, as well any of the additional or optional ingredients, components, or limitations described herein.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All documents incorporated herein by reference in their entirety are only incorporated herein to the extent that they are not inconsistent with this specification.

All percentages, parts and ratios are based upon the total weight of the composition of the present invention, unless otherwise specified. All such weights as they pertain to the listed ingredients are based on the active level and, therefore, do not include carriers or by-products that may be included in commercially available materials, unless otherwise specified.

The terms "grow" or "growth" as used herein with respect to hair means the growth or regrowth of hair. Accordingly, the terms "growth" and "regrowth" are used interchangeably with respect to growing hair or respect to actives for growing hair.

The term "safe and effective amount" as used herein means an amount of a compound or composition such as a topical or system active sufficient to significantly induce a positive benefit, for example, hair growth, but low enough to avoid serious side effects, i.e., to provide a reasonable benefit to risk ratio, within the scope of sound judgment of the skilled artisan.

As used herein, the terms "visual inspection" or "visually inspected" means that a human viewer can visually discern the presence of: i) solid or droplet particles in a solution; or ii) hair or hair growth, in each case, with the unaided eye (excepting standard corrective lenses adapted to compensate for near-sightedness, farsightedness, or stigmatism, or other corrected vision) in lighting at least equal to the illumination of a standard 75 watt incandescent white light bulb at a distance of about 0.25 meter.

The term "pharmaceutically acceptable addition salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formulas (I and II) are able to form. The compounds of formula (I and II) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formulas (I and II) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I and II) are able to form. Examples of such forms are e.g. hydrates, alcoholates and the like.

For therapeutic use, salts of the compounds of formulas (I and II) are those wherein the counterion is pharmaceutically acceptable.

In certain embodiments, the present invention as disclosed herein may be practiced in the absence of any compound or element (or group of compounds or elements) which is not specifically disclosed herein.

The composition of the present invention is useful for growing hair. The composition comprises a hair growth active and a $C_8$-$C_{24}$ alcohol ester of a carboxylic acid.

The composition of the present invention is also useful for preventing hair loss and thinning hair.

Hair Growth Compound

The compositions of the present invention further comprise one or more of a hair growth or hair regrowth compound represented by the Formulas I or II:

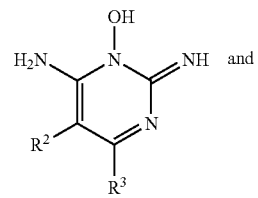

Formula I

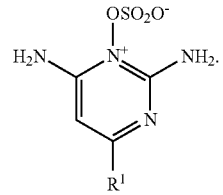

Formula II and mixtures thereof.

$R^1$ is hydrogen or —$N(R^3)(R^4)$. Each $R^3$ and $R^4$ individually is selected from the group consisting of hydrogen, lower alkyl, lower alkenyl, lower aralkyl, and lower cycloalkyl, and taken together $R^3$ and $R^4$ may be a heterocyclic moiety selected from the group consisting of aziridinyl, azetidinyl, pyrrolidinyl, piperidino, hexahydroazepinyl, heptamethylenimino, octamethylenimino, morpholino, and 4-lower-alkylpiperazinyl, each of said heterocyclic moieties having attached as substituents on the carbon atoms 0 to 3 lower alkyl groups, hydroxy or alkoxy, and wherein $R^2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl; tautomers thereof and pharmacologically acceptable acid addition salts thereof (such as sulfate salts thereof).

The amount of the compound of the above Formulas I and/or II is a safe and effective amount for promoting hair growth. In certain embodiments, the compound of Formulas I and/or II is present at a concentration of from 0.1% (or about 0.1%) to 15% (or about 20.0%) of the preparation, or optionally, from 0.5% (or about 0.5%) to 10% (or about 10%), or optionally, from 0.5% (or about 0.5%) to 5% (or about 5%), by weight of the composition.

Listed below are definitions of various terms used to describe the compounds of Formulas I and/or II.

The term "lower alkyl" refers to straight or branched chain hydrocarbon groups containing typically 1 to 6 carbon atoms, and more typically 1 to 3 carbon atoms.

Examples of suitable lower alkyl groups include methyl, ethyl and propyl. Examples of branched alkyl groups include isopropyl and t-butyl. Examples of suitable alkoxy groups are methoxy, ethoxy and propoxy.

The "lower cycloalkyl" groups typically contain 3-6 carbon atoms and include cyclopropyl, cyclobutyl, cyclopentyl and cyclohexyl.

The "lower alkenyl" groups typically contain 2-6 carbon atoms and include ethenyl, propenyl and butenyl. The "lower cycloalkenyl" groups typically contain 3-6 carbon atoms and include cyclopropenyl, cyclobutenyl, cyclopentenyl and cyclohexenyl.

The term "lower aryl" refers to monocyclic or multi-ring aromatic hydrocarbon groups typically containing 6 to 14 carbon atoms in the ring portion, such as phenyl, 2-naphthyl, 1-naphthyl, 4-biphenyl, 3-biphenyl, 2-biphenyl, and diphenyl groups.

Examples of halo groups are Cl, F, Br and I.

The Mixture of $C_8$-$C_{24}$ Alkyl Lactates

The compositions of the present invention also include a mixture of $C_{12}$-$C_{15}$ alkyl lactates.

The mixture of $C_{12}$-$C_{15}$ alkyl lactates refers to compositions comprising $C_{12}$ alkyl lactates, $C_{13}$ alkyl lactates, $C_{14}$ alkyl lactates, and $C_{15}$ alkyl lactates at a ratio of $C_{12}$ alkyl lactates to $C_{13}$ alkyl lactates of about 1:1 to about 1:2; a ratio of $C_{13}$ alkyl lactates to $C_{14}$ alkyl lactates of about 1:1 to about 1:2; and a ratio of $C_{14}$ alkyl lactates to $C_{15}$ alkyl lactates of about 1:1 to about 1:2 (other components such as $C_{12}$ alcohols, $C_{13}$ alcohols, $C_{14}$ alcohols, and/or $C_{15}$ alcohols may, optionally, be present in the mixture). Such mixtures are available from Ashland (NJ, USA).

In certain embodiments, the mixture $C_{12}$-$C_{15}$ alkyl lactates is present in the composition in an amount of from 0.5% (or about 0.5%) to 10% (or about 10%), optionally, from 1.0% (or about 1.0%) to 5% (or about 5%), or, optionally, from 1.5% (or about 1.5%) to 3% (or about 3%), by weight of the composition.

Viscosity Modifying Agent

In certain embodiments, the compositions of the present invention further comprise a viscosity modifying agent comprising a cellulose or cellulose derivative (including the anionic carboxymethylcellulose and the nonionic celluloses mentioned below).

More specifically, in certain embodiments where the composition comprises from about 5% to about 30%, optionally from about 10% to about 25%, or, optionally, from about 15% to about 25%, by weight, alcohol (as described herein and, in certain embodiments, ethanol); from about 0 to about 40%, optionally from about 5% to about 30%, or optionally about 10% to about 20%, by weight, glycol (such as propylene glycol or pentylene glycol); from about 0.1 to about 10%, optionally from about 0.5% to about 5%, or optionally about 1% to about 3%, by weight, $C_8$-$C_{24}$ alcohol ester of a carboxylic acid (as described herein); and from about 1% to about 15%, optionally from about 2% to about 10%, or optionally from about 2% to about 5%, by weight, minoxidil (or a pharmacologically acceptable acid addition salts thereof), storage stability of the compositions at temperatures both above 30° C. and below 5° C. can be achieved by incorporating a mixture of $C_{12}$-$C_{15}$ is alkyl lactates as the $C_8$-$C_{24}$ alcohol ester of a carboxylic acid in combination with at least one cellulose derivative (including the anionic carboxymethylcellulose and the nonionic celluloses mentioned below)

Useful cellulose of cellulose derivatives include, but are not limited to, nonionic celluloses or cellulose derivatives such as hydroxylalkyl cellulose polymers (e.g., hydroxyl $C_1$-$C_3$ alkyl cellulose polymers) and alkyl hydroxylalkyl cellulose polymers (e.g., $C_9$-$C_{16}$ alkyl hydroxyl $C_1$-$C_3$ alkyl cellulose polymers) such as hydroxyethyl cellulose, hydroxypropyl cellulose, cetyl hydroxyethyl cellulose; methyl cellulose and its derivatives such as hydroxymethylcellulose derivatives such as hydroxypropyl methylcellulose (HPMC) and hydroxybutyl methyl cellulose and anionic cellulose derivatives such as methyl cellulose (or derivatives thereof such as carboxymethyl cellulose (CMC)).

In certain embodiments, from 0.1% (or about 0.1%) to 20% (or about 20%), optionally, from 0.5% (or about 0.5%) to 15% (or about 15%), or, optionally, from 1% (or about 1%) to 5% (or about 5%), by weight of the composition, of the mixture of $C_{12}$-$C_{15}$ alkyl lactates is incorporated with from 0.01% (or about 0.01%) to 5% (or about 5%), or, optionally from 0.1% (or about 0.1%) to 4% (or about 4%), optionally, from 1% (or about 1%) to 3% (or about 3%), or, optionally from 0.5% (or about 0.5%) to 2% (or about 2%), by weight of the composition, of the at least one cellulose or cellulose derivative.

Without being limited by theory, it is believed that embodiments of the compositions of the present invention comprising from about 0.1% to about 20% (optionally, from about 0.5% to about 15%, or optionally, from about 1% to about 10%) by weight of a pharmaceutically acceptable addition salt of the hair growth or hair regrowth compounds of formulas I or II (in certain embodiments, the pharmaceutically acceptable addition salt of minoxidil); from about 0.5% to about 10% (optionally, from about 2% to about 7.5%) by weight of an oil phase or oily compound; and from about 0 to about 25% (optionally from about 1% to about 25%, or optionally from about 5% to about 20%) by weight of a $C_2$-$C_4$ alcohol (optionally ethanol), collectively, increase the difficulty of achieving storage stability. The present inventor has discovered that achieving storage stability is facilitated by incorporating a viscosity modifying agent comprising a mixture of $C_{12}$-$C_{15}$ alkyl lactates as the $C_5$-$C_{24}$ alcohol ester of a carboxylic acid in combination with at least one cellulose or cellulose derivative (including the anionic carboxymethylcellulose and the nonionic celluloses mentioned above).

Term "oil phase" or "oily phase" means any non-polar liquid phase which is immiscible with aqueous liquids (or not water-soluble). In certain embodiments, the oil phase comprises at least one oily compound such as the $C_8$-$C_{24}$ alcohol ester of a carboxylic acid (e.g., cetyl lactate, myristyl lactate) and, optionally, long chain fatty acids such as the steareth-10. Other components that may be comprised in the oil phase are volatile oils and non-volatile oils. As used herein the term "oily", means a hydrophobic and water immiscible.

The term "storage stable" or "storage stability" when referring to a composition of the present invention, means a composition (such as a solution, emulsion or microemulsion) which is uniform and homogeneous and which is not separated into two or more distinct phases upon visual inspection after the composition is stored in closed, airtight glass containers for at least 1 week, optionally at least 7 weeks, at a constant temperature of 40° C. in a standard laboratory oven (for example, a Fisher Scientific Isotemp Oven, Model 655F Wadesboro, N.C., USA, and for at least 3 days at a constant temperature of 5° C. in a standard laboratory refrigerator (for example, VWR refrigerator model R411GA16, manufactured by Kendro Laboratory Products, Asheville, N.C., USA,). The above described storage of the composition at 40° C. and at 5° C. can occur either separately or sequentially. Relative humidity is not controlled for during such storage since the storage takes place in closed glass containers whose walls and closures are impervious to the passage of water vapor.

According to the ICH Harmonized Tripartite Guideline "Stability Testing of New Drug Substances and Products Q1A(R2), storage at 25° C. for a period of time is indicative of stability of the formulation or therapeutic agent for twice this period of time at 5° C. See also Drug Stability, Principles and Practices, Third Edition, Jens T. Cartensen, Chris T. Rhodes, published by Marcel Dekker. Assuming an Arrhenius dependence for the degradation kinetics, an increase of 10° C. accelerates the effective period of storage by approximately a factor of 2. Hence, the ICH guidelines estimate that 13 weeks at 40° C. is equivalent to 2 years at room temperature (or 25° C.). This conversion therefore allows that 13 weeks storage at 40° C. and 60% relative humidity is similar to a 2 years shelf-life for a formulation at 25° C.

In addition to the viscosity modifying agents mentioned above, other viscosity modifying agent may further be added to impart viscosity and/or shear thinning properties to the compositions of the present invention. Suitable additional viscosity enhancing agents include, but are not limited to:

(a) ionic polymers including cationic polymers such as quaternary ammonium compounds, polyquaternium compounds and quaternium silicone compounds and anionic polymers such as carboxymethyl cellulose (CMC) (the same or different from that referenced above).

Examples of suitable quaternary ammonium compounds include, but are not limited to, polyquaternium compounds; distearyldimonium chloride; dipalmitoylethylhydroxyethylmonium chloride; dioleoylethyl dimethyl ammonium methosulfate; dioleoylethyl hydroxyethylmonium methosulfate; dilinolamidopropyldimonium chloride; dioleylethyl hydroxyethylmonium chloride; dipalmitoylethyldimonium chloride; cocodimonium hydroxypropyloxyethyI cellulose; lauryldimonium hydroxypropyloxyethyl cellulose; stearyldimonium hydroxyethyl cellulose; stearyldimonium hydroxypropyl oxyethyl cellulose; quaternium proteins such as hydroxypropyltrimonium hydrolyzed collagen, lauryldimonium hydroxypropyl hydrolyzed collagen, cocodimonium hydroxypropyl hydrolyzed collagen, stearyltrimonium hydroxyethyl hydrolyzed collagen, stearyidimonium hydroxypropyl hydrolyzed collagen, hydroxypropyltrimonium hydrolyzed keratin, cocodimonium hydroxypropyl hydrolyzed hair keratin, cocodimonium hydroxypropyl hydrolyzed keratin, hydroxypropyltrimonium gelatin, hydroxypropyltrimonium hydrolyzed casein; quaternary starches such as hydroxypropyltrimonium hydrolyzed wheat starch, hydroxypropyltrimonium hydrolyzed corn (maize) starch, hydroxypropyltrimonium hydrolyzed potato starch, hydroxypropyltrimonium hydrolyzed amylopectin; Quaternium-33 (quaternary lanolin); quaternary guar derivatives such as guar hydroxypropyltrimonium chloride, hydroxypropyl guar hydroxypropyltrimonium chloride; quaternary natural and plant actives (sugar derivatives) such as choline; and mixture thereof.

Examples of suitable polyquaternium compounds include, but are not limited to, Polyquaternium 6, Polyquaternium 7 (co-polymer of diallylmethyl ammonium chloride), Polyquaternium 10 (quaternized hydroxyethylcellulose polymer), Polyquaternium 11, Polyquaternium 16, Polyquaternium 22, Polyquaternium 28, Polyquaternium 29 (quaternary chitosan), Polyquaternium 37, Polyquaternium 42, Polyquaternium 44, Polyquaternium 50 and mixtures thereof. Commercial examples include Polymer JR type from Amerchol such as Polyquaternium 10, Cosmedia Ultra 300 or Cosmedia SP (Polyquaternuim 37) from BASF, or cationic guar gum known Guar hydroxypropyl trimonium chloride with trade name N-Hance and AquatCat from Ashland.

The cationic polymers may also include the quaternized products of graft polymers from organopolysiloxanes and polyethyl oxazolines described in U.S. Pat. Nos. 5,472,689 and 5,747,016, both of which patents are hereby incorporated by reference.

In addition to the carboxymethyl celluloses, anionic polymers can include homopolymers and copolymers of carboxymethyl monomers, and in particular homopolymers and copolymers of (meth) acrylic acid, such as: polyacrylic acid, acrylic acid/ethyl acrylate copolymers, acrylic acid/polyallyl sucrose copolymers and mixtures thereof (b) nonionic polymers such as polysaccharides or polysaccharide derivatives and in particular: celluloses and derivatives thereof, such as hydroxyalkyl cellulose polymers and alkyl hydroxyalkyl cellulose polymers such as hydroxyethyl cellulose, hydroxypropyl cellulose, cetyl hydroxyethyl cellulose; methyl cellulose and its derivatives such as hydroxymethylcellulose derivatives such as hydroxypropyl methylcellulose (HPMC) and hydroxybutyl methyl cellulose (the same or different from that referenced above); natural or synthetic gums and their derivatives, and in particular xanthan gum, guar gum, and pectin; starch and starch derivatives; chitin such as chitosan; xyloglucan; polyvinylalcohol; polyvinylpyrrolidone; or their derivatives.

Nonionic polymers also include poloxamers having the following formula:

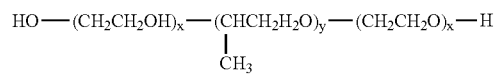

where "x" represents the average number of PEO units and is an integer of from about 80 to about 140, optionally about 90 to about 120, or optionally from about 95 to a about 110; "y" represents the average number of PPO units is an integer of from about 40 to 80, optionally from about 50 to about 70 and the ratio of "x" to "y" is no greater than 4:1 (or about 4:1), optionally 3:1 (or about 3:1), optionally 2.8:1 (or about 2.8:1), optionally 2:1 (or about 2:1), or optionally 1:1 (or about 1:1), yet the ratio of "x" to "y" is at least 2:1 (or about 2:1), or optionally 3:1 (or about 3:1). Suitable examples of such poloxamers are described below:

| Poloxamer | Pluronic (supplied by BASF) | "y" (Average No. of PPO units) | "x" (Average No. of PEO units) |
|---|---|---|---|
| 338 | F108 | 50.3 | 132.7 |
| 407 | F127 | 65.2 | 100.2 |

In certain embodiments, the viscosity modifying agent is a cationic polymer such as polyquaternium-37. Such a viscosity modifying agent is for example commercially available from Cognis under the trademark name Ultragel 300 and from Ciba under the trademark name Salcare.

In certain embodiments, the viscosity modifying agent is an anionic polymer such as carboxymethyl cellulose. Such a viscosity modifying agent is for example commercially available from CP Kelco under the trademark name FinnFix or Dow Chemical under the tradename Walocel™.

In certain embodiments, the viscosity modifying agent is nonionic polymer such as poloxamer. Such a viscosity modifying agent is for example commercially available from BASF under the trademark name Pluronic.

In certain embodiments, the viscosity modifying agent is nonionic polymer such as hydroxypropylmethyl cellulose. Such a viscosity modifying agent is for example commercially available from Dow Chemical under the trademark name Methocel E10M premium CR HPMC.

In certain embodiments, the viscosity modifying agent is selected from (or the group consisting of), but not limited to, cationic polymers such as polyquaternium 37, polyquaternium 7, polyquaternium 4, polyquternoium 10; anionic polymers such as carboxymethylcellulose; non-ionic polymers such as hydroxypropylmethyl cellulose and poloxamer 407; or mixtures thereof.

In certain embodiments, the viscosity modifying agent is a mixture of a nonionic polymer as described herein and an ionic polymer, including the cationic and anionic polymers, as described herein.

In certain embodiments, the viscosity modifying agent is a mixture of two or more of polymers selected from (or, the group consisting of), but not limited to, cationic polymers such as polyquaternium 37, polyquaternium 7, polyquaternium 4, polyquternoium 10; anionic polymers such as carboxymethylcellulose; non-ionic polymers such as hydroxypropylmethyl cellulose and poloxamer 407; or mixtures thereof.

In certain embodiments, the viscosity modifying agent is a mixture of two or more of the carboxymethylcellulose, hydroxypropylmethyl cellulose and poloxamer 407.

The viscosity modifying agent(s) is (are) employed in an amount sufficient to provide the inventive composition with a viscosity such that when the composition is applied to the scalp and/or hair, the composition does not easily drip down the scalp or hair fibers in a fluid-like manner and it is able to hold the fibers together during the treatment or application period.

At the same time, the viscosity of the inventive composition is such that it is easy to spread or apply onto the hair fibers in a uniform manner as well as permit easy combing of hair.

The viscosity modifying agent (s) may be used in concentrations ranging from about 0.1% to about 10.0% by weight, optionally from about 0.5% to about 5.0% by weight, or optionally from about 1.0% to 5.0% by weight of the total composition.

In certain embodiments, the compositions of the present invention have a viscosity of from about 50 cps to about 30000 cps, optionally from about 100 cps to about 15000 cps, or optionally from about 500 cps to about 10000 cps as measured using a Brookfield RV (spindle 4, speed 6 RPM at 1 minute following the temperature equilibration at 25° C.±1° C.).

In certain embodiments, the compositions of the present invention have a viscosity of less than about 10000 cps, or optionally from about 50 cps to about 8000 cps, optionally from about 100 cps to about 6000 cps as measured using a Brookfield RV (spindle 4, speed 6 RPM at 1 minute following the temperature equilibration at 25° C.±1° C.).

Alternatively, in certain embodiments, where the composition comprises from about 5% to about 65%, optionally from about 10% to about 60%, or optionally, from about 15% to about 35%, by weight, alcohol (as described herein and, in certain embodiments, ethanol); from about 0 to about 40%, optionally from about 5% to about 30%, or optionally about 10% to about 20%, by weight, glycol (such as propylene glycol or pentylene glycol); from about 0.1 to about 10%, optionally from about 0.5% to about 5%, or optionally about 1% to about 3%, by weight, $C_8$-$C_{24}$ alcohol ester of a carboxylic acid (as described herein and, in certain embodiments, cetyl lactate, myristyl lactate or mixtures thereof); and from about 1% to about 15%, optionally from about 2% to about 10%, or optionally from about 2% to about 5%, by weight, minoxidil (or a pharmacologically acceptable acid addition salts thereof), storage stability of the compositions at temperatures both above 30° C. and below 5° C. can be achieved by incorporating a viscosity modifying agent comprising a nonionic hydroxypropylmethyl cellulose and a high molecular weight carboxymethyl cellulose at a ratio of the nonionic hydroxypropylmethyl cellulose to the high molecular weight carboxymethyl cellulose of greater than 1:1 (or about 1:1), optionally 3:1 (or about 3:1). In certain embodiments, the ratio of nonionic hydroxypropylmethyl cellulose to high molecular weight carboxymethyl cellulose is no greater than 10:1 (or about 10:1), wherein the total concentration of the nonionic hydroxypropylmethyl cellulose and high molecular weight carboxymethyl cellulose is from 0.5% (or about 0.5%) to 3% (or about 3%), optionally from 0.85% (or about 0.85%) to 1.25% (or about 1.25%), by weight of the total composition.

The term "high molecular weight carboxymethyl cellulose" means a carboxymethyl cellulose having: i.) a carboxymethyl degree of substitution (C.M.D.S.) (which is average number of ionizable carboxymethyl ether groups per repeating anhydroglucose chain unit of the cellulose molecule) of from 0.4 (or about 0.4) to 1.5 (or about 1.5), optionally from 0.6 (or about 0.6) to 0.9 (or about 0.9), or optionally 0.7 (or about 0.7); ii.) an average degree of polymerization of from about 2000 to about 4000, optionally from about 2500 to about 3500, or optionally 3200 (or about 3200); and iii) a weight average molecular weight of from about 600,000 to about 800,000, optionally from about 650,000 to about 750,000, or optionally from about 675,000 to about 730,000. Suitable high molecular weight carboxymethyl cellulose are supplied by Ashland (Wilmington, Del.) under the tradenames Aqualon® CMC 7HF, Aqualon® CMC-7H4, Aqualon® CMC-7H3S, Aqualon® CMC-7HOF and Aqualon® CMC-7H. In certain embodiments, the high molecular weight carboxymethyl cellulose is Aqualon® CMC 7HF.

In certain embodiments, the viscosity modifying agents also imparts shear thinning properties to the compositions of the present invention. Shear thinning is a term used in rheology to describe non-Newtonian fluids which have decreased viscosity when subjected to shear strain. As used herein, the "shear-thinning viscosity" of the compositions of the present invention refers to the pseudo plastic-like property of the compositions such that the compositions upon application of a shear stress (e.g., from pumping or pouring, dispensing during manufacture or distribution/application of the compositions) changes viscosity and becomes less thick and flows more like water. As used herein, the "yield stress value" refers to the minimum amount of shear stress (such as, as a result of application by pumping, pouring or other distribution/application of the compositions) necessary before the flow of the compositions begin or, alternatively, the point where the viscous modulus G" of the composition becomes larger than the storage modulus G'. In certain embodiments the compositions of the present invention have a shear-thinning viscosity and a yield stress value such that when the composition is applied to the mammal skin e.g. scalp, the shear created by the application action (e.g., by either finger(s) or an applicator such as a roller or a dropper, or a brush) will allow the composition to thin and spread out evenly over the treatment surface. Once applied the composition regains its higher viscosity which avoids drips and runs on the scalp or face.

The shear thinning property of the compositions of the present invention can also be described in terms the composition's shear thinning index (as described below).

Shear Thinning Measurement Procedure

Rheological measurements were performed (TA Instruments ARES G2 Rheometer). Yield stress values were measured by performing strain sweeps at 1 rad/s, and taking the yield stress value as the point where the viscous modulus G" became larger than the storage modulus G' upon increasing oscillatory stress. Frequency sweeps were performed from 100 to 0.1 rad/s at a strain in the linear viscoelastic regime. Flow curve steps were performed by stepping the shear rate from 0.1 to 1000 s$^{-1}$ and allowing the torque to reach a steady value for each point.

$$\text{Shear thinning index} = \frac{\text{a first viscosity}}{\text{a second viscosity}}$$

Wherein the first viscosity is measurement obtained from the first shear rate of 1 s$^{-1}$ and the second viscosity is the measurement obtained from the second shear rate of 450 s$^{-1}$.

The above mentioned rheological properties for the composition of Example 1 were determined to be as follows:

| | Yield stress value (Pa · s) | Viscosity at 1 s$^{-1}$ (Pa · s) | Viscosity at 450 s$^{-1}$ (Pa · s) | Shear Thinning Index |
|---|---|---|---|---|
| Composition of Example 1 | 0.93 | 7.3 | 0.33 | 22.1 |

In certain embodiments, the compositions of the present invention have a viscosity at a shear rate of 1 s$^{-1}$ of from about 0.1 Pa·s to about 15 Pa·s, or optionally from about 1 Pa·s to about 10 Pa·s.

In certain embodiments, the compositions of the present invention have a viscosity at a shear rate of 450 s$^{-1}$ of from about 0.01 Pa·s to about 1 Pa·s, or, optionally from about 0.1 Pa·s to about 0.5 Pa·s.

In certain embodiments, the compositions of the present invention have a yield stress value of from about 0.01 Pa·s to about 5 Pa·s, optionally from about 0.1 Pa·s to about 2.0 Pa·s, or optionally from about 0.1 Pa·s to about 0.95 Pa·s.

In certain embodiment, the compositions of the present invention have a shear thinning index of 10 or more, optionally, of 20 or more, optionally from about 10 to about 500, optionally from about 20 to about 100, or optionally from about 20 to about 50.

Pharmaceutically Acceptable Topical Carriers

The topical compositions useful in this invention contain formulations suitable for topical application to skin and scalp. The term "topical" as employed herein relates to the use of a composition along with a suitable pharmaceutical carrier, and applied according to the method of the present invention at the site of hair loss, reduced hair growth or baldness for exertion of local action. Accordingly, such topical compositions useful in the methods of the present invention include those pharmaceutically acceptable forms in which the compound is applied externally by direct contact with the skin surface to be treated.

The compositions of the present invention contain the $C_8$-$C_{24}$ alcohol ester of a carboxylic acid and the hair growth compound in a pharmaceutically acceptable topical carrier. The phrase "pharmaceutically acceptable", as used herein, denotes compatibility with the active contemplated herein, including the hair growth actives. The pharmaceutically acceptable topical carriers are also compatible with the skin, scalp and any keratinous substrates.

Accordingly, the pharmaceutically acceptable topical carrier is formulated such that upon mixing with the $C_8$-$C_{24}$ alcohol ester of a carboxylic acid, the combined mixture is a multiple phase mixture with the $C_8$-$C_{24}$ alcohol ester of a carboxylic acid forming one phase and the pharmaceutically acceptable topical carrier forming separate phase. In certain embodiments, the multiple phase mixture is a bi-phasic mixture.

In certain embodiments, the pharmaceutically acceptable topical carrier of the present invention includes one or more solubilizers for the hair growth compound. Suitable solubilizers include, but are not limited, monohydric or polyhydric simple alcohols, including, but not limited to, water, $C_1$-$C_3$ alcohols (such as methanol, ethanol, n-propanol, isopropanol), n-butanol such as 1-butanol, n-hexanol, 2-ethyl-1-hexanol, polyhydric alcohols (such as ethylene glycol, propylene glycol, polypropylene glycol [e.g., polyethylene glycol 200 (PEG 200), polyethylene glycol 400 (PEG 400)], pentylene glycol, the butanediol isomers, 1,5 pentane diol, 1,2,6-trihydroxyhexane, 1 2-ethyl-1,3-hexanediol, 1,7-heptanediol, or glycerin); ether alcohols, such as, for example, 1-methoxy-2-propanol, 3-ethyl-3-hydroxymethyloxetan, tetrahydrofurfuryl alcohol, ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, diethylene glycol or dipropylene glycol; solubilizers such as xylene, chlorobenzene, ethyl acetate, butyl acetate, diethylene glycol dimethyl ether, dipropylene glycol dimethyl ether, ethylene glycol monomethyl or monoethyl ether acetate, diethylene glycol ethyl and butyl ether acetate, propylene glycol monomethyl ether acetate, 1-methoxypropyl-2-acetate, 3-methoxy-n-butylacetate, propylene glycol diacetate, N-methylpyrrolidone and N-methylcaprolactam, tocopheryl polyethylene glycol succinate (TPGS), dimethylformamide (DMF), dimethylacetamide (DMA), caprylcaproyl macrogol 8-glyceride (Labrasol) or mixtures of any of the above mentioned solubilizers.

In certain embodiments, the solubilizer of the present invention is selected from one or more $C_1$-$C_3$ alcohol(s) such as ethanol, n-propanol, isopropanol; one or more polyhydric alcohol(s) such as propylene glycol, polypropylene glycol, pentylene glycol, glycerin; ethyl acetate and mixtures thereof. In certain embodiments, the solubilizer of the present invention comprises ethanol, isopropanol, pentylene glycol, propylene glycol, ethyl acetate, polyethylene glycol and mixtures thereof.

In certain embodiments, the one or more solubilizer(s) is present in the composition in an amount of from about 0.1% to about 60%, optionally, from about 0.1% to about 50%, or, optionally, from about 0.1% to about 40%, by weight of the total composition.

In certain embodiments, the one or more $C_1$-$C_3$ alcohol(s) are present in the composition in an amount of from about 0.1% to about 40%, optionally, from about 1% to about 30%, or, optionally, from about 10% to about 25%, by weight of the total composition.

In certain embodiments, the one or more polyhydric alcohol(s) is present in the composition in an amount of from about 0.1% to about 40%, optionally, from about 1% to about 30%, or, optionally, from about 5% to about 25%, by weight of the total composition.

In certain embodiments, the compositions of the present invention further comprise water in an amount of from about 5% to about 60%, optionally, from about 10% to about 50%, or, optionally, from about 20% to about 40%, by weight of the total composition. In certain embodiments, to obtain "clear" compositions, monohydric (such as ethanol, propanol, isopropanol and mixtures thereof) and dihydric (such as propylene glycol, butylene glycol, pentylene glycol and mixtures thereof) alcoholic solubilizers are incorporated at a total concentration of from about 20% to about 90%, optionally from about 30% to about 80%, optionally from about 35% to about 80%, optionally, from about 40% to about 75%, or, optionally, from about 50% to about 70%, by weight of the total composition.

The term "clear" as used herein means a solution or gel composition free of or substantially free of particles or droplets greater than 2 microns (optionally, 1 micron). The term "substantially free" as used with respect to particles or droplets greater than 2 microns (optionally, 1 micron) means solution or gel compositions having less than 20, optionally 10, or optionally 5 of particles or droplets greater than 2 microns (optionally, 1 micron) per 0.5 mm$^2$ field of view when viewed by a high magnification microscope (such as an Hirox RH-2000E with MXB-5000REZ lens).

The term clear also means a solution or gel composition free of or substantially free of turbidity when visually inspected. The term "turbidity" as used herein means the cloudiness or haziness of a fluid caused by individual particles (suspended solids or liquids) that are generally invisible to the unaided eye. Fluids can contain suspended solid or liquid matter consisting of varying particle size. While some suspended material will be large enough and heavy enough to settle rapidly to the bottom of the container (or separate into distinct layers) if a liquid sample is left to stand, very small particles will settle (or separate out) only very slowly or not at all if the sample is regularly agitated or the particles are colloidal. These small solid or liquid particles cause the liquid to appear turbid.

One property of such solid or liquid particles is that they will scatter a light beam focused on them. This light scattering effect is considered a good measure of turbidity in water. Turbidity measured this way uses an instrument called a Turbidimeter with the detector setup to the side of the light beam. The more particles floating in water, the more light is scattered toward the detector and the higher the value of detected light. A lower value of detected light indicates a clearer or less cloudy solution. The units of turbidity from a calibrated Turbidimeter (such as a Laboratory Turbidimeter HACH Model 2100N operating at ambient temperature [20° C.]) are called Nephelometric Turbidity Units (NTUs). A clear formulation is defined as a formulation with an NTU of less than 10 (or about 10), optionally less than 8 (or about 8), or optionally less than 6 (or about 6).

In certain embodiments, where the composition comprises a $C_{12}$-$C_{18}$ alkyl lactate, the clarity of the composition is dependent upon the concentration of the $C_{12}$-$C_{18}$ alkyl lactates. The relationship can be defined in terms of the following "relative dielectric constant index" (RI) equation:

$$RI = (D1/D2)/\% \text{ concentration of } C_{12}\text{-}C_{18} \text{ alkyl lactate (as percentage of total composition)}$$

Where:
D1=the total dielectric constant of all non-aqueous solvents
D2=the total dielectric constant of aqueous solvents/the conc.

The present inventor has found that compositions having an RI value of greater than 0.15 were determined to be clear compositions.

In certain embodiments, the hair growth compounds are dissolved in or contain as auxiliary components one or more solubilizing acid(s) which dissolve minoxidil (and other compounds of formulas I and II) such as citric acid, acetic acid, succinic acid, maleic acid, benzoic acid, lactic acid, tartaric acid, barbituric acid, protocatechuic acid, gallic acid, 5-nitro-2-furoic acid, alpha-keto acids and mixtures thereof. In certain embodiments, the solubilizing acids are selected from citric acid, lactic acid, alpha-keto acids or mixtures thereof.

When used, the lactic acid or lactate may be selected from the group consisting of lactic acid, salts of lactic acid, pro-drugs of lactic acid, and mixtures thereof. The salts of lactic acid may include, but is not limited to, alkali salts and alkaline earth salts. In certain embodiments, the lactate is selected from the group consisting of lactic acid, lithium lactate, sodium lactate, potassium lactate, magnesium lactate, calcium lactate, zinc lactate, manganese lactate, and the like, and mixtures thereof. In other embodiments, the lactate is selected from the group consisting of lactic acid, sodium lactate, potassium lactate, magnesium lactate, calcium lactate, zinc lactate, manganese lactate, and mixtures thereof. In still further embodiments, the lactate is lactic acid. Additionally or alternatively, an alpha-keto acid may be used as the auxiliary component acid. In certain embodiments, the alpha-keto acid is a pyruvic acid selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, salts thereof, prodrugs thereof, and mixtures thereof.

When present in the compositions of the present invention, the one or more solubilizing acid(s) is present in an amount suitable for dissolving the hair growth compound. In certain embodiments, the one or more solubilizing acid(s) is present in the composition in an amount from about 0.1% to about 10%, optionally, from about 0.5% to about 7.5%, or, optionally, from about 1.0% to about 5.0%, by weight of the composition.

In certain embodiments, the pharmaceutically acceptable topical carrier of the present invention includes one or more emulsifier(s). Emulsifiers may be nonionic, anionic, cationic, and/or polymeric. Examples of suitable emulsifiers include, but are not limited to, those typically identified as such in the art of personal care and cosmetic formulations, e.g., cationic emulsifiers such as distearyldimonium chloride, non-ionic emulsifiers such as steareth-2, steareth-21, glyceryl stearate, glyceryl laurate, lecithin, glycol stearate, glycol stearate SE, glycol distearate, sorbitan esters, such as sorbitan trioleate, sorbitan oleate, sorbitan stearate, ceteth-2, PEG-30 dipolyhydroxystearate, PEG-4 dilaurate, Laureth-4, PEG-7 glyceryl cocoate, polysorbate 85, PEG-100 stearate, PEG-8 laurate, PEG-8 oleate, polysorbate 60, polysorbate 80, cetearyl glucoside, Oleth-20, Ceteth-20, PEG-25 hydrogenated castor oil stearamide MEA, stearyl alcohol, cetyl alcohol; anionic emulsifiers such as potassium cetyl phosphate; polymeric emulsifiers such as acryloyldimethyltaurate/VP copolymers, and the like and mixtures of any of the above emulsifiers.

In certain embodiments, the emulsifier of the present invention is selected from the group consisting of steareth-2, glyceryl stearate, polysorbate 60, polysorbate 80, stearyl alcohol, cetyl alcohol and mixtures thereof. In certain embodiments, the emulsifier of the present invention is steareth-2, polysorbate 60 and mixtures thereof.

In certain embodiments, the one or more emulsifier(s) is present in the composition in an amount from about 0.1% to about 15%, optionally, from about 0.1% to about 10%, or, optionally, from about 0.1% to about 5%, by weight of the total composition.

In certain embodiments, the pharmaceutically acceptable topical carrier can be in any product form, including ointments, pastes, gels, jellies, serums, aerosol and non-aerosol sprays, foams, creams, lotions, solutions, toners, suspensions, leave-on conditioners, and the like. The term "ointment" embraces formulations (including creams) having oleaginous, absorption, water-soluble and emulsion-type bases, e.g., petrolatum, lanolin, polyethylene glycols, as well as mixtures of these. A more detailed discussion of the specific carriers and additional components useful in the compositions of the present invention can be found in U.S. Patent Publication 2008/0145331 to Bruning et al., herein incorporated by reference in its entirety. In one embodiment, the pharmaceutically-acceptable topical carrier constitutes from about 50% to about 99.99%, by weight, of the composition or optionally from about 80% to about 95%, by weight, of the composition.

Alternatively, rinse off carrier forms such as shampoos, cream rinses, conditioners, cleansers and cleansing lotions may also be used.

Vesicles

The compositions of the present invention also comprise one or more vesicles. In certain embodiments, the vesicles are liquid vesicles. In certain embodiments, the vesicles are non-phospholipid vesicles. FIG. 1 is a picture of a microscopic field of view as obtained using a Olympus BX51 Microscope (as described below) showing the liquid vesicles contained in the composition of Example 1 (below).

In certain embodiments, the vesicle has an average diameter of from about 0.05 μm to about 20 μm, optionally from about 0.1 μm to about 15 μm, or optionally from about 0.3 to about 10 μm. Measurement of the average diameter of the vesicles of the present invention is described in more detail below. In certain embodiments, the vesicles are multilayer (i.e., have at least two layers) where the layers have a layer thickness of about 0.01 μm to about 2 μm, preferably about 0.05 μm to about 1 μm.

The following procedure can be used to determine the average diameter of vesicles in the microscopic field of view as depicted in FIG. 1:

A transmission microscope equipped with conventional CCD camera technology (i.e., Olympus BX51 Microscope, Magnification 100×) was used to obtain a magnified field of view to acquire a microscopic image of the vesicles. The vesicles within the magnified field of view of the microscope are detected and their corresponding diameters were measured by the accompanying image analysis software of the microscope (i.e., analySIS image software, Olympus Soft Imaging Solutions GmbH).

The statistical analysis output for the magnified field view of FIG. 1 that was obtained using the above described image analysis software is shown in Table A below. It was found that average diameter of the vesicles in the magnified field of view of FIG. 1 was about 0.7 μm±0.83 μm.

TABLE A

| Parameter | Value |
| --- | --- |
| Count (the total number of vesicles detected in the magnified field of view of FIG. 1) | 2918 |
| Average Diameter | 0.70 μm |
| Minimum Diameter | 0.13 μm |
| Maximum Diameter | 10.81 μm |
| Standard Deviation of Average Diameter | 0.83 μm |

The vesicle shown in FIG. 1 has an average diameter of 0.7 μm, with a minimum diameter of 0.13 μm and maximum diameter of 10.8 μm.

Figure 2:
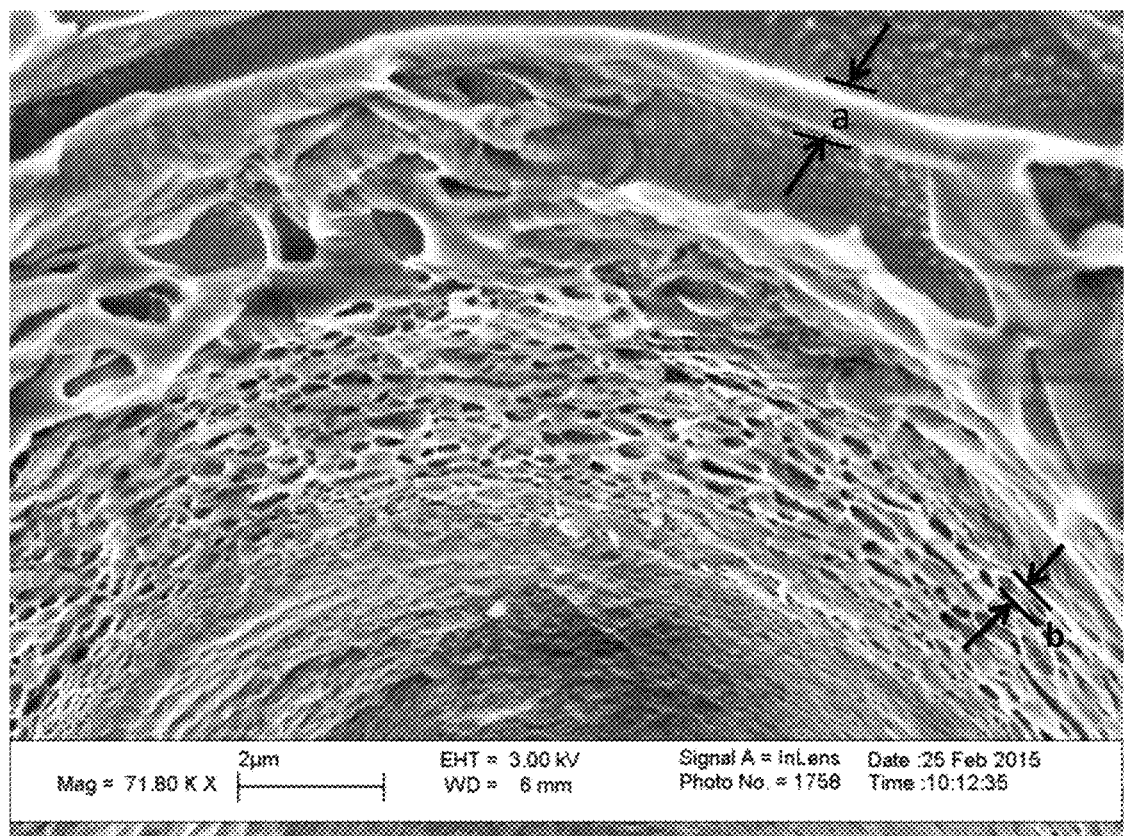
FIG. 2 is a freeze-fractured SEM (scanning electron microscopy) picture of partial cross-section of one of the liquid vesicles contained in the composition of Example I (below)

FIG. 2 shows a freeze-fractured SEM (scanning electron microscopy) picture of partial cross-section of one of the liquid vesicles contained in the composition of Example I (below).

FIG. 2 also depicts the multiple layers of the liquid vesicle, showing layer thicknesses "a" and "b". The layer thickness "a" is about 0.4 μm and the layer thickness "b" is about 0.2 μm as measured using the "2 μm" measurement scale depicted at the bottom the picture of FIG. 2.

The $C_8$-$C_{24}$ alcohol ester of a carboxylic acid and/or the hair growth compound can be present in either the vesicle or the pharmaceutical acceptable topical carrier, or in both the vesicle and the pharmaceutical acceptable topical carrier.

Optional Ingredients

Additional Actives

In certain embodiments, the compositions of the present invention may, optionally, further include active agent selected from the group consisting of additional hair growth actives, anti-acne agents, antimicrobial agents, anti-fungal agents, antibiotic or antiseptic agents, antipsoriatic agents, anti-viral agents, anti-seborrea agents, anti-dandruff agents, active agents for treating keratosis pilaris, anti-inflammatory agent, vasodilators, UV absorbers and anti-cancer agents.

In certain embodiments, the compositions of the present invention include additional hair growth actives. In certain embodiments, the additional hair growth active selected from a group of compounds known to promote hair growth and available as drugs, such as diazoxide, pinacidil, bimatoprost, finasteride, a type 2 5-alpha-reductase inhibitor, and dutasteride, a type 1- and 2-5-alpha-reductase inhibitor, as well as flutamide, bicalutamide, pregnane derivatives, progesterone derivatives, experimental agents such as FCE 28260 and the like. Spironolactone and other diuretics may also be utilized as it is indicated for women in some cases (also known as aldactone: an aldosterone receptor antagonist). Also useful as hair growth agents are azole antifungals as mentioned below. Examples of suitable azole antifungals include, but are not limited to, miconazole, ketoconazole, econazole, itraconazole, sertaconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, their pharmaceutically acceptable salts, and combinations thereof.

Also useful in certain embodiments as the additional hair growth active are herbal remedies that may have 5-alpha-reductase inhibitory action or actives with inhibitory activity for dihydrotestosterone (DHT) or otherwise induce hair growth may include: saw palmetto, □-sitosterol and *Pygeum africanum*. Other additional hair growth actives that may have such activity are beta-sisterol, sepicontrol and licorice, gamma-linolenic acid and other unsaturated fatty acids, zinc, copper and their salts, *Cotinus coggygria* extract, green tea catechin (−)-epigallocatechin gallate (EGCG) and other polyphenols, and the like. Grape seed, apple seed, apple juice, blackberry, millet seed, marione extract, cysteine, *Thuja orientalis* extract, *Polygonum multiflorum* thunberg extract, Espinosilla extract, *Hibiscus rosa sinensis* flowers, *Murraya koenigii*, hinokitiol, and barley extracts may also be potential additional hair growth actives, although they are not thought to be very common or satisfactory in achieving satisfactory hair growth results.

The additional hair growth active may also include agents or natural extracts that activate or inhibit the Wnt or beta-catenin pathway such as valproic acid (VPA), lithium salts, dihydroquercetin-glucoside (DHQG), epigallocatechin gallate-glucoside, agents or natural extracts that can accelerate hair follicle growth such as placental growth factor (PlGF), *reflexa* (*C. reflexa*) etc, epidermal growth factor (EGF), vascular epithelia growth factor (VEGF), fibroblast growth factors (FGF) such as FGF 5, or FGF9, BMP (bone morphogenetic protein) inhibitors such as 6-(4-(2-(piperidin-1-yl)ethoxy)phenyl)-3-(pyridin-4-yl)pyrazolo[1,5-a]pyrimidine, dorsomorphinor mixtures thereof. Inhibitors for TGF-β such as proanthocyanidines like procyanidine B from the flavonoids can also be used.

Additional hair growth actives may also include Prostaglandin D$_2$ inhibitors, or Agents with antiandrogenic properties Cortexolone 17a-propionate.

Other additional hair growth actives include prostaglandine analogues licke vsprostol, or latanoprost, bimatoprost or their deriavtives, extract of red deer antler, *Adiantum capillus-veneris* Linn. (*A. capillus-veneris*), ginsenoside F2) and mixtures thereof.

Mixtures of any of the above described additional hair growth actives can also be used.

An anti-acne agent is a compound that has been approved by the U.S. Food and Drug Administration for the topical treatment of acne. Examples of suitable anti-acne agents include, but are not limited to, salicylic acid, benzoyl peroxide, sulphur, retinoic acid, *Candida bombicola*/glucose/methyl rapeseedate ferment, peat water, resorcinol, silt, peat, permethin, azelaic acid, clindamycin, adapalene, erythromycin, sodium sulfacetamide, minocycline, tetracycline, oxycycline, sodium sulfacetamide, dapsone, retinoid such as isotretinoin, tretinoin, ethinyl estradiol, norgestimate, nicotinamide, and their derivatives, and combinations thereof.

Antimicrobial agents are compounds that kill microorganisms or prevent or inhibit their growth or reproduction. Examples of suitable antimicrobial agents include, but are not limited to: ethanol, propanol, betains, benzalkonium chloride, benzethonium chloride, lauric arginayte, sugarquat, methyl benzethonium chloride, cetypyridiunium chloride, 2,4,4',-trichloro-2-hydroxy diphenyl ether (Triclosan), parachlorometa xylenol (PCMX), Iodopropynyl butylcarbamate, diazolidinyl urea, chlorhexidene digluconate, chlorhexidene acetate, chlorhexidene isethionate, chlorhexidene hydroclloride, hexetidine, Quaternium 15, triclocarbon, polyhexamethylene biguanide, cetylpyridium chloride, imidazolidinyl urea, diazolidinyl urea, 3-iodo-2-propynyl-N-butylcarbamate, 2-methyl-4-isothiazolin-3-one, dimethyl dimethyl hydantoin, (5-chloro-2-(2,4-dichlorophenoxy)phenol, monolaurin glyceryl laurate, *Camellia sinensis, Candida bombicola*/glucose/methyl rapeseedate ferment, hydrogen peroxide, phenol, poloxamer 188, PVP-iodine, thiourea, natural antimicrobial agents, such as cinnamon oil, cinnamaldehyde, lemongrass oil, clove oil, saw palmetto extract, thyme oil white, thyme oil red, thymol, tea tree oil, *Pinus pinaster* bark extract, rosemary leaf extract, grape seed extract, and betel oil, silver containing compounds, such as silver nitrate, silver lactate, silver citrate, and silver zeolite, antimicrobial fatty acid ester of a polyhydric alcohol, a fatty ether of a polyhydric alcohol and alkoxylated derivatives thereof, and combinations thereof.

Antimicrobial agent includes anti-fungal agents such as an azole. Examples include, but are not limited to, miconazole, ketoconazole, econazole, itraconazole, sertaconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, their pharmaceutically acceptable salts, and combinations thereof.

Antimicrobial agents include antibiotics or antiseptics. Examples of these include, but are not limited to, mupirocin, neomycin sulfate bacitracin, polymyxin B, 1-ofloxacin, tetracyclines such as chlortetracycline hydrochloride, oxytetracycline-10 hydrochloride and tetrachcycline hydrochloride, clindamycin phosphate, gentamicin sulfate, metronidazole, hexylresorcinol, methylbenzethonium chloride, phenol, quaternary ammonium compounds, tea tree oil, and combinations thereof.

Examples of antipsoriatic agents include, but are not limited to, corticosteroids (e.g., betamethasone dipropionate, betamethasone valerate, clobetasol propionate, diflorasone diacetate, halobetasol propionate, triamcinonide, dexamethasone, fluocinonide, fluocinolone acetonide, halcinonide, triamcinolone acetate, hydrocortisone, hydrocortisone venerate, hydrocortisone butyrate, aclometasone dipropionte, flurandrenolide, mometasone furoate, and methylprednisolone acetate), methotrexate, cyclosporine, calcipotriene, anthraline, shale oil, elubiol, ketoconazole, coal tar, salicylic acid, zinc pyrithione, selenium sulfide, hydrocortisone, sulfur, 2,2'-sulfanediylbis(4,6-dichlorophenol) (bithionol), 6-hydroxy-1,3-benzoxathiol-2-one (tioxolone), 2,7-dimethylthianthrene (mesulfen), menthol, and pramoxine hydrochloride, and combinations thereof.

Examples of anti-viral agents include, but are not limited to, imiquimod, podofilox, podophyllin, interferon alpha, acyclovir, famcyclovir, valcyclovir, reticulos and cidofovir.

Anti-seborrea or sebum inhibition agents such as elubiol.

Examples of anti-dandruff agents include but are not limited to zinc pyrithione, elubiol, coal tar, salicylic acid or selenium sulfide, sulphur, ketoconazole, corticosteroids such as fluocinolone acetonide, caffeine and combinations thereof.

Active agents for treating keratosis pilaris. Examples of active agents for treating keratosis pilaris include but are not limited to fluoracil, Imiquimod, aminolevulinic acid and combinations thereof.

Examples of anti-inflammatory agents, include, but are not limited to, non-steroidal and steroidal anti-inflammatory agents such as corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, betamethasone dipropionate, and triamcinolone, and combinations thereof. Examples of non-steroidal anti-inflammatory agents include but not limited to COX inhibitors, LOX inhibitors, and p38 kinase inhibitors, immunosuppressant agents such as cyclosporin, and cytokine synthesis inhibitors. Other natural anti-inflammatories include, but are not limited to, extracts of feverfew, boswellia, aloe vera, chamomille, lavender, soy, or oats, beta-glucan, and totarol. Other active agents include, but are not limited to, wound healing enhancing agents such as calcium alginate, collagen, recombinant human platelet-derived growth factor (PDGF) and other growth factors, ketanserin, iloprost, prostaglandin $E_1$ and hyaluronic acid (including cross-linked hyaluronic acid); scar reducing agents such as mannose-6-phosphate; analgesic agents; debriding agents such as papain, and enzymatic debriding agents; and anesthetics such as lidocaine and benzocaine. In one embodiment, the composition comprises one or more of menthol, camphor, an antihistamine, or a local anesthetic such as tetracaine, lidocaine, prilocaine, benzocaine, bupivacaine, mepivacaine, dibucaine, etidocaine, butacaine, cyclomethycaine, hexylcaine, proparacaine, and lopivacaine, capsaicin, or oatmeal.

Examples of vasodilators include: methylnicotinate, arginine, hexylnicotinate, papaverine, tolazoline, acetylcholine, sodium nitroprusside, nitroglycerine, adensosine or a combination thereof.

Examples of suitable UV absorbers include benzophenone, bornelone, butyl paba, cinnamidopropyl trimethyl ammonium chloride, disodium distyrylbiphenyl disulfonate, paba, potassium methoxycinnamate, and mixtures thereof.

Examples of anti-cancer agents include: AG-490; aldesleukin; alemtuzumab; alitretinoin; allopurinol; altretamine; amifostine; An-238; anastrozole; arsenic trioxide; asparaginase; BCG Live (Bacillus Calmette-Guerin); bevazizumab; bexarotene; bleomycin; busulfan; calusterone; capecitabine; capecitabine; carboplatin; carmustine; celecoxib; cetuximab; chlorambucil; cisplatin; cladribine; cyclophosphamide; cyclophosphamide; cytarabine; dactinomycin; darbepoetin alfa; dasatinib; daunorubicin; daunorubicin, daunomycin; denileukin diftitox; dexrazoxane; docetaxel; doxorubicin; dromostanolone propionate; Elliott's B Solution; endostatin; epirubicin; epoetin alfa; estramustine; etoposide phosphate; etoposide, VP-16; exemestane; filgrastim; floxuridine; fludarabine; fluorouracil; FTI-2777; fulvestrant; gefitinib; gemcitabine; gemcitabine; gemtuzumab ozogamicin; GGTI-298; goserelin acetate; gossypol; hydroxyurea; ibritumomab; idarubicin; idarubicin; ifosfamide; imatinib mesylate; interferon alfa-2a; interferon alfa-2b; IL-2; IL-12; irinotecan; letrozole; leucovorin; levamisole; lomustine; meclorethamine; nitrogen mustard; megestrol acetate; melphalan, L-PAM; mercaptopurine, 6-MP; mesna; methotrexate; methoxsalen; mitomycin C; mitotane; mitoxantrone; nandrolone phenpropionate; nofetumomab; oprelvekin; oxaliplatin; paclitaxel; pamidronate; pegademase; pegaspargase; pegfilgrastim; pentostatin; pentostatin; pipobroman; plicamycin; mithramycin; porfimer sodium; PP2; procarbazine; quinacrine; rasburicase; RC3095; rituximab; sargramostim; streptozocin; talc; tamoxifen; temozolomide; teniposide, VM-26; testolactone; thioguanine, 6-TG; thiotepa; topotecan; toremifene; tositumomab; trastuzumab; tretinoin, ATRA; U0126; uracil mustard; valrubicin; vinblastine; vincristine; vinorelbine; wortmanin; and zoledronate.

In certain embodiments, the active are water soluble actives. Suitable examples include, but are not limited to, sulfonated molecules such as, for example sodium sulfate, water soluble vitamins (or their derivatives) such as thiamine, riboflavin (B2), nicotinic acid, niacin, biotin (B7), folate (B9), cobalamin, panthenol, panththenic acid, choline, ascorbic acid; water soluble proteins such as keratins, collagens, elastins, wheat germ proteins, wheat proteins, soy proteins, protease, serum proteins, hair proteins; water soluble peptides and polypeptides such as amino acids derived from protein hydrolysis such as those described in U.S. Pat. No. 6,419,913, herein incorporated by reference; plant extracts obtained from water extract process such as feverfew extracts and soy extracts; ethanol soluble such actives include depilating agents such as calcium thioglycolate, potassium thioglycolate and external analgesics and local anesthetics such as benzocaine.

In certain embodiments, the active is oil soluble. Suitable examples include, but are not limited to, vitamins or their derivatives such as vitamin E, vitamin $D_3$, vitamin A, retinol, retinoids or melatonin.

Mixtures of the above additional actives can also be used.

Some embodiments of the present invention further include color stabilizers. Suitable color stabilizers include, but are not limited to, butylated hydroxytoluene or IRGANOX® 1010, a hindered phenol available from Ciba-Geigy, Hawthorne, N.Y., U.S. A. IRGANOX® 1010 is tetrakis[methylene(3, 5-di-tert-butyl-4-hydroxyhydrocinnamate)] methane. In certain embodiments, the color stabilizer is used in an amount of about 0.05 to about 1.0% by weight based on the total weight of the compositions of the present invention.

Non-Ionic Lipid

In certain embodiments, the compositions of the present invention further include a non-ionic lipid. The non-ionic lipid can form micro- or nano-vesicles in an emulsion of any types such as oil in water (o/w), water in oil (w/o), oil in water in silicone.

In certain embodiments, the non-ionic lipids include non-ionic lipid such as glyceryl monoesters having a fatty acid chain containing from about 3 to about 50 carbon atoms, and optionally from about 10 to about 18 carbon atoms; glyceryl diesters having a fatty acid chain containing from about 5 carbon atoms to about 25 carbon atoms, and optionally from about 10 carbon atoms to about 18 carbon atoms; alkoxylated alcohols; alkoxylated alkyl phenols; alkoxylated acids; alkoxylated amides; alkoxylated sugar derivatives; alkoxylated derivatives of natural oils or waxes; polyoxyethylene polyoxypropylene block copolymers;

polyoxyethylene ether fatty acids having a fatty acid chain containing from about 10 carbon atoms to about 18 carbon atoms; steroids; fatty acid esters of alcohols where the fatty acid is straight or branched chain having from about 10 carbon atoms to about 20 carbon atoms and the alcohol is straight or branched chain having 1 to 10 carbon atoms; and mixtures thereof, wherein, optionally, the alkoxylated lipids are alkoxylated with ethylene oxide or propylene oxide, or optionally ethylene oxide.

Non-limiting examples of suitable glyceryl monoesters include, but are not limited to, glyceryl caprate, glyceryl caprylate, glyceryl cocate, glyceryl erucate, glyceryl hydroxysterate, glyceryl isostearate, glyceryl lanolate, glyceryl laurate, glyceryl linolate, glyceryl myristate, glyceryl oleate, glyceryl PABA, glyceryl palmitate, glyceryl ricinoleate, glyceryl stearate, glyceryl thiglycolate, and mixtures thereof, optionally glyceryl laurate, glyceryl myristate and mixtures thereof.

Non-limiting examples of suitable glyceryl diesters include, but are not limited to, glyceryl dilaurate, glyceryl dioleate, glyceryl dimyristate, glyceryl disterate, glyceryl sesuioleate, glyceryl stearate lactate, and mixtures thereof, optionally glyceryl dilaurate, glyceryl dimyristate and mixtures thereof.

Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and mixtures thereof.

Non-limiting examples of suitable steroids include, but are not limited to, cholesterol, betasitosterol, bisabolol, and mixtures thereof.

Non-limiting examples of suitable fatty acid esters of alcohols include isopropyl myristate, aliphati-isopropyl n-butyrate, isopropyl n-hexanoate, isopropyl n-decanoate, isproppyl palmitate, octyidodecyl myristate and mixtures thereof.

In certain embodiments, the non-ionic lipid in the compositions of the invention have the structure shown in formula I below:

$$R_5-(OCH_2CH_2)_y-OH \quad \text{Formula I}$$

wherein $R_5$ is a branched or unbranched alkyl group having from about 6 to about 22 carbon atoms and y is between about 4 and about 100, and preferably, between about 10 and about 100. A preferred alkoxylated alcohol is the species wherein R s is a lauryl group and y has an average value of 23, which is known by the CTFA name "laureth 23" and is available from ICI Americas, Inc. of Wilmington, Del. under the tradename, "BRIJ 35."

In other embodiments, the alkoxylated alcohol is an ethoxylated derivative of lanolin alcohol. Lanolin alcohol is a mixture of organic alcohols obtained from the hydrolysis of lanolin. An example of an ethoxylated derivative of lanolin alcohol is laneth-10, which is the polyethylene glycol ether of lanolin alcohol with an average ethoxylation value of 10.

In an embodiment, the alkoxylated alcohol is polyoxypropylene polyoxyethylene alkyl ether, the structure of which is shown schematically in formula II below:

$$R(OCHCH_2)_x(OCH_2CH_2)_qOH \quad \text{Formula II}$$
$$\text{with } CH_3 \text{ branch}$$

wherein x:q is about 2:2 to about 38:37. An exemplary member of this class of materials is the material known by the CTFA name "PPG-12-Buteth-16," which conforms to structure II above wherein R is a butyl group, x has an average value of 12 and y has an average value of 16. This material is available from Amerchol Corp. of Edison, N.J. under the tradena me, "UCON Fluid 50-HB-660."

Another type of non-ionic lipids include alkoxylated alkyl phenols, which generally conform to the structure of formula III:

$$R_6-C_6H_4-(OCH_2CH_2)_z-OH \quad \text{Formula III}$$

wherein $R_6$ is a branched or unbranched alkyl group having about 6 to about 22 carbon atoms and z is between about 7 and 120, and preferably, between about 10 and about 120. An especially preferred member of this class of materials is the species wherein $R_6$ is a nonyl group and z has an average value of about 14. This material is known by the CTFA name "nonoxynol-14" and is available under the tradename, "MAKON 14" from the Stepan Company of Northfield, Ill.

Another type of non-ionic lipids include alkoxylated acids, which are esters of an acid, most usually a fatty acid, with a polyalkylene glycol. An exemplary material of this class has the CTFA name "PEG-8 laurate," and the following structure shown in formula IV.:

$$CH_3(CH_2)_{10}-C(=O)-(OCH_2CH_2)_8-OH \quad \text{Formula IV}$$

Another type of non-ionic lipids includes the alkoxylated amides that may conform to one or both of structures V or VI shown below:

$$R'-C(=O)-N\big((CH_2CH_2O)_m-H\big)\big((CH_2CH_2O)_b-H\big) \quad \text{Formula V}$$

$$R'-C(=O)-NH-(CH_2CH_2O)_n-H \quad \text{Formula VI}$$

wherein n is from about 8 to about 100 and the sum of m plus b is from about 8 to about 100. An exemplary member of this class is known by the CTFA name "PEG-6 Cocoamide," which conforms generally to structure V wherein R'CO represents the fatty acids derived from coconut oil and n has an average value of about 6.

Another type of non-ionic lipids includes the alkoxylated sugar derivatives. An exemplary member of this class, which is known by the CTFA name "Polysorbate 20," is a mixture of laurate esters of sorbitol and sorbitol anhydrides, consisting predominately of the monoester, condensed with about 20 moles of ethylene oxide. This material is available under the tradename "TWEEN 20" from ICI Americas of Wilmington, Del.

Another example of an alkoxylated sugar derivative useful in the compositions of the invention is PEG-20 methylglucose sesquistearate, which is the polyethyleneglycol ether of the sesquiester of methyl glucose and stearic acid, contains an average of 20 moles of ethylene oxide, and is available under the tradename, "Glucamate SSE-20" from the Amerchol Corp. of Edison, N.J.

Another type of non-ionic lipids includes the alkoxylated derivatives of natural oils and waxes. Examples of this class of material include PEG-40 lanolin, PEG-40 castor oil and PEG-40 hydrogenated castor oil.

Another type of non-ionic lipids includes polyoxyethylene polyoxypropylene block copolymers. These materials are generally known by the CTFA name, "Poloxamer" and conform to the structure VII.:

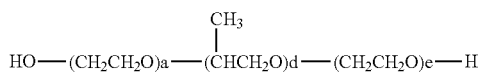

Formula VII wherein a:d:e is from about 2:16:2 to about 98:67:98. Exemplary members of this class of materials useful in the compositions of the invention are "Poloxamer 101" and "Poloxamer 182," in which a, d, and e have average values of 2, 16 and 2 and 8, 30 and 8, respectively.

In certain embodiments, the non-ionic lipids include polyoxyethylene $C_4$-$C_{26}$ fatty ethers, glyceryl diesters, and mixtures thereof. Optionally, non-ionic lipids include polyoxyethylene $C_{10}$-$C_{18}$ fatty ethers such as polyoxyethylene stearyl ether (steareth-10), polyoxyethylene myristyl ether, and polyoxyethylene lauryl ether, glyceryl dilaurate, glyceryl dimystate, glyceryl distearate, and mixtures thereof, wherein, optionally, each ether has from about 5 to about 10 oxyethylene units. Optionally, non-ionic lipid is a polyoxyethylene stearyl ether (steareth-10).

In certain embodiments, the non-ionic lipid is present in the composition in an amount from about 0.1% to about 20%, optionally, from about 0.2% to about 15%, or, optionally, from about 0.5% to about 10%, by weight of the composition.

When present, the concentration of the polyoxyethylene $C_4$-$C_{26}$ fatty ether is from about 0.1% to about 15%, optionally, from about 0.2% to about 10%, or, optionally, from about 0.3% to about 5%, by weight of the composition.

The Admixture

In certain embodiments, the compositions of the present invention further include an admixture comprising: 1) an acid selected from the group consisting of intermediates of the Kreb cycle, non-Kreb cycle intermediate alpha keto acid, derivatives thereof and mixtures thereof; and/or 2) an antioxidant and 3) a mixture of saturated and unsaturated fatty acids or a source of of such mixture of saturated and unsaturated fatty acids.

In certain embodiments, the admixture is present in the composition at a concentration of from 0.1% (or about 0.1%) to 20% (or about 20%), optionally from 0.1% (or about 0.1%) to 30% (or about 30%), optionally from 0.5% (or about 0.5%) to 20% (or about 20%), or optionally from 0.5% (or about 0.5%) to 10% (or about 10%), by weight, of the admixture.

Acid Component of Admixture

In certain embodiments, the acid component of the admixture of the present invention is selected from the group consisting of intermediates of the Kreb cycle, non-Kreb cycle alpha keto acids, derivatives thereof and mixtures thereof.

Kreb cycle (or Citric acid cycle) intermediates useful herein, include, but are not limited to, 2-oxoglutarate, fumarate, succinate, oxaloacetate, citrate, cis-aconitate, isocitrate, oxalosuccinate, alpha-ketoglutarate, L-malate, esters thereof, ethers thereof or salts thereof and mixtures thereof.

In other embodiments, the acid component is a non-Kreb cycle intermediate alpha-keto acid (or 2-oxoacid). The alpha-keto acid (or 2-oxoacid) has the keto group adjacent to the carboxylic acid. By "non-Kreb cycle intermediate", as used herein, means a chemical, compound or intermediate not produced by the Kreb cycle or Citric Acid cycle. In certain embodiments, suitable non-Kreb cycle alpha-keto acids include, but are not limited to, pyruvic acid (alpha-ketopropionic acid), alpha-ketoisovaleric acid, alpha-ketoisocaproic acid, salts thereof and mixtures thereof. It should be understood, however, that in addition to these alpha-keto acids, the unqualified term "alpha-keto acids" further includes, but is not limited to, alpha ketoglutaric acid.

In certain embodiments, the alpha-keto acid useful as the acid component is a pyruvic acid. Pyruvic acid suitable for use in the present invention may be selected from the group consisting of pyruvic acid, salts of pyruvic acid, prodrugs of pyruvic acid, and mixtures thereof. In certain embodiments, the salts of pyruvic acid may be alkali salts and alkaline earth salts. In certain embodiments, the pyruvic acid is selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, and mixtures thereof.

In other embodiments, the pyruvic acid is selected from the group of salts consisting of sodium pyruvate, potassium pyruvate, magnesium pyruvate, calcium pyruvate, zinc pyruvate, manganese pyruvate, and the like, and mixtures thereof. In still other embodiments, the pyruvic acid is sodium pyruvate.

Without being limited by theory, it is believed that the acid component acts as the energy source component for the admixture. In certain embodiments, the acid is present in the composition in an amount of from 0.01% (or about 0.01%) to 99.98% (or about 99.98%), or optionally 10% (or about 10%) to 90% (or about 90%), or optionally from 20% (or about 20%) to 70% (or about 70%), or optionally from 25% (or about 25%) to 50% (or about 50%), or optionally from 30% (or about 30%) to 40% (or about 40%), or optionally about 33%, by weight, of the admixture.

Antioxidant Component of the Admixture

Antioxidants, as mentioned above, are also present as a component of the admixture of the present invention. Generally, antioxidants are substances which inhibit oxidation or suppress reactions promoted by oxygen or peroxides. Without being limited by theory, it is believed that antioxidants, or, optionally, lipid-soluble antioxidants, can be absorbed into the cellular membrane to neutralize oxygen radicals and thereby protect the hair follicles from oxidative damage. In certain embodiments, the antioxident component may be selected from the group consisting of all forms of Vitamin A including lycopene, lutein, retinal and 3,4-didehydroretinal, all forms of carotene such as alpha-carotene, beta-carotene (beta, beta-carotene), gamma-carotene, delta-carotene, all forms of Vitamin C (D-ascorbic acid, L-aseorbic acid), all forms of tocopherol such as Vitamin E (alpha-tocopherol, 3,4-dihydro-2,5,7,8-tetramethyl-2-(4,8,12-trimethyltridecyl)-2H-1-benzopy ran-6-ol), beta-tocopherol, gamma-tocopherol, delta-tocopherol, tocoquinone, tocotrienol, and Vitamin E esters which readily undergo hydrolysis to Vitamin E such as Vitamin E acetate and Vitamin E succinate, and Vitamin E salts such as Vitamin E phosphate, prodrugs of Vitamin A, carotene, Vitamin C, and Vitamin E, salts of Vitamin A, carotene, Vitamin C, and Vitamin E, and the like, flavonoids and mixtures thereof. Flavonoids useful in the present can be found in U.S. Pat. No. 6,051,602 to Bissett, herein incorporated by reference. In other embodiments, the antioxidant is selected from the group of lipid-soluble antioxidants consisting of Vitamin A, beta-carotene, tocopherol, and mixtures thereof. In still other embodiments, the antioxidant is tocopherol Vitamin E or Vitamin E acetate. In yet other embodiments, the antioxidant is a polyphenol such as resveratrol or epigallocatechin gallate.

In certain embodiments, the antioxidant component is present in the composition in an amount of from 0.01% (or about 0.01%) to 99.98% (or about 99.98%), or optionally 10% (or about 10%) to 90% (or about 90%), or optionally from 20% (or about 20%) to 70% (or about 70%), or optionally from 25% (or about 25%) to 50% (or about 50%), or optionally from 30% (or about 30%) to 40% (or about 40%), or optionally about 33%, by weight, of the admixture.

The Fatty Acid Mixture Component or Fatty Acid Mixture Source Component of the Admixture The admixture of the present invention also contains as a component thereof a mixture of saturated and unsaturated fatty acids, free or bound, or a source of such saturated and unsaturated fatty acids useful in providing a readily available source of nutrients to hair follicles Suitable mixtures of saturated and unsaturated fatty acids may be derived from animal and vegetable fats and waxes, mammalian or fish egg materials, prodrugs of saturated and unsaturated fatty acids useful in the present compositions, and mixtures thereof. The fatty acids in the fatty acid mixture may be in the form of mono-, di-, or triglycerides, or free fatty acids, or mixtures thereof.

In one embodiment, the fatty acid mixture of saturated and unsaturated fatty acids has a composition similar to that of human fat and comprises the following fatty acids: butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, dihomolinoleic acid, arachidonic acid, behenic acid, lignoceric acid and gadoleic acid. Typically, butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, and gadoleic acid are present in the mixture in about the following percentages by weight, respectively: about 0.2%-0.4% butyric acid, about 0.1% caproic acid, about 0.3%-0.8% caprylic acid, about 2.2%-3.5% capric acid, about 0.9%-5.5% lauric acid, about 2.8%-8.5% myristic acid, about 0.1%-0.6% myristoleic acid, about 23.2%-24.6% palmitic acid, about 1.8%-3.0% palmitoleic acid, about 6.9%-9.9% stearic acid, about 36.0%-36.5% oleic acid, about 20%-20.6% linoleic acid, about 7.5-7.8% linolenic acid, about 1.1%-4.9% arachidic acid, about 2%-3% dihomolinoleic acid, about 7%-9% arachidonic acid, about 3%-4% behenic acid, about 11%-13% lignoceric acid and about 3.3%-6.4% gadoleic acid.

In another embodiment, the fatty acid mixture of saturated and unsaturated fatty acids has a composition similar to chicken fat and comprising the following fatty acids: lauric acid, myristic acid, myristoleic acid, pentadecanoic acid, palmitic acid, palmitoleic acid, margaric acid, margaroleic acid, stearic acid, oleic acid, linoleic acid, linolenic acid, arachidic acid, and gadoleic acid. Optionally, lauric acid, myristic acid, myristoleic acid, pentadecanoic acid, palmitic acid, palmitoleic acid, margaric acid, margaroleic acid, stearic, oleic acid, linoleic acid, linolenic acid, arachidic acid, and gadoleic acid are present in the mixture in about the following percentages by weight, respectively: about 0.1% lauric acid, about 0.8% myristic acid, about 0.2% myristoleic acid, about 0.1% pentadecanoic acid, about 25.3% palmitic acid, about 7.2% palmitoleic acid, about 0.1% magaric acid, about 0.1% heptadecenoic acid, about 6.5% stearic acid, about 37.7% oleic acid, about 20.6% linoleic acid, about 0.8% linolenic acid, about 0.2% arachidic acid, and about 0.3% gadoleic acid.

In certain other embodiments, the fatty acid mixture of saturated and unsaturated fatty acids has a composition similar to lecithin. Lecithin (phosphatidylcholine) is a phosphatide found in all living organisms (plants and animals) and is a significant constituent of nervous tissue and brain substance. Lecithin is a mixture of the diglycerides of stearic acid, palmitic acid, and oleic acid, linked to the choline ester of phosphoric acid. The product of commerce is predominantly soybean lecithin obtained as a by-product in the manufacturing of soybean oil. Soybean lecithin contains by weight palmitic acid 11.7%, stearic acid 4.0%, palmitoleic acid 8.6%, oleic acid 9.8%, linoleic acid 55.0%, linolenic acid 4.0%, $C_{20}$ to $C_{22}$ acids (includes arachidonic acid) 5.5%. Lecithin may be represented by the formula: $C_8H_{17}O_5NR^9R^{10}$ wherein each of $R^9$ and $R^{10}$ are, independently, selected from the group consisting of stearic acid, palmitic acid, and oleic acid.

In certain other embodiments, the fatty acid mixture of saturated and unsaturated fatty acids has a composition similar to egg yolk. The composition (by weight) of the most prevalent fatty acid mixture in egg yolk can be broken into by weight:

A. unsaturated fatty acids such as oleic acid (about 47%), linoleic acid (about 16%), palmitoleic acid (about 5%), and linolenic acid (about 2%); and B. saturated fatty acids: such as palmitic acid (about 23%), stearic acid (about 4%), and myristic acid (about 1%).

Egg yolk is also a source of lecithin.

The above fatty acid mixtures (or fatty acid mixture sources) and percentages of fatty acids present in the various fatty acid mixture (or sources thereof) are provided as examples. The exact type of fatty acid present in the fatty acid mixture (or mixture sources) and the exact amount of fatty acid employed in the fatty acid mixture (or mixture sources) may be varied in order to obtain the result desired in the final product and such variations are now within the capabilities of those skilled in the art without the need for undue experimentation.

In certain embodiments of the present invention, the fatty acid mixture or fatty acid mixture source comprising at least 7, optionally at least 14, and optionally at least 22, unsaturated or saturated fatty acids selected from the group consisting of, but not limited to, butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, gadoleic acid, pentadecanoic acid, margaric acid, margaroleic acid, behenic acid, dihomolinoleic acid, arachidonic acid and lignoceric acid. Other useful fatty acids can be found in U.S. Pat. No. 4,874,794 to Adachi et al., herein incorporated by reference.

In certain embodiments, the fatty acid mixture in the admixture is obtained or sourced from oil mixtures. For example, cottonseed oil has a 2:1 ratio of polyunsaturated to saturated fatty acids. Its fatty acid profile generally consists of 70% unsaturated fatty acids including 18% monounsaturated (oleic), 52% polyunsaturated (linoleic) and 26% saturated (primarily palmitic and stearic). More specifically, cottonseed oil has fatty acids present in the mixture in about the following percentages by weight, respectively: about 0.5-2.0% myristic acid, about 17.0-29.0% palmitic acid, less than about 1.5% palmitoleic acid, about 1.0-4.0% stearic acid, about 13.0-44.0% oleic acid, about 40.0-63.0% linoleic acid, and about 0.1-2.1% linolenic acid.

Cocoa butter has fatty acids present in a mixture at about the following percentages by weight, respectively: at least about 0.1% myristic acid, about 0.5-26.3% palmitic acid, at least about 0.4% palmitoleic acid, about 0.5-33.8% stearic acid, about 0.5-34.4% oleic acid, and about 0.5-3.1% linoleic acid.

Olive oil was determined in one study to have fatty acids present in a mixture at about the following percentages by weight, respectively: about 0.5-9.0% palmitic acid, at least about 0.4% palmitoleic acid, about 0.5-2.7% of stearic acid, about 0.5-80.3% oleic acid, about 0.5-6.3% of linoleic acid, and about 0.5-0.7% linolenic acid.

Oils suitable for use as a fatty acid mixture source include, but are not limited to, *Adansonla digitata* oil; apricot (*Prunus armeniaca*) kernel oil; *Argania spinosa* oil; *Argemone mexicana* oil; avocado (*Persea gratissima*) oil; babassu (*Orbignya olelfera*) oil; balm mint (*Melissa officinalis*) seed oil; bitter almond (*Prunus amygdalus amara*) oil; bitter cherry (*Prunus cerasus*) oil; black currant (*Ribes nigrum*) oil; borage (*Borago officinalis*) seed oil; brazil (*Bertholletia excelsa*) nut oil; burdock (*Arctium lappa*) seed oil; butter; *Calophyllum tacamahaca* oil; *Camellia kissi* oil; *Camellia oleifera* seed oil; canola oil; caraway (*Carum carvi*) seed oil; carrot (*Daucus carota sativa*) oil; cashew (*Anacardium occidentale*) nut oil; castor oil benzoate; castor (*Ricinus communis*) oil; cephalins; chaulmoogra (*Taraktogenos kurzii*) oil, chia (*Salvia hispanica*) oil; cocoa (*Theobrama cocao*) butter; coconut (*Cocos nucifera*) oil; cod liver oil; coffee (*Coffea arabica*) oil; corn (*Zea mays*) germ oil; corn (*Zea mays*) oil; cottonseed (*Gossypium*) oil; cucumber (*Cucumis sativus*) oil; dog rose (*Rosa canina*) hips oil; egg oil; emu oil; epoxidized soybean oil; evening primrose (*Oenothera biennis*) oil; fish liver oil; *Gevuina avellana* oil; goat butter; grape (*Vitis vinifera*) seed oil; hazel (*Croylus americana*) nut oil; hazel (*Corylus aveilana*) nut oil; human placental lipids; hybrid safflower (*Carthamus tinctorius*) oil; hybrid sunflower (*Helianthus annuus*) seed oil; *Isatis tinctoria* oil; job's tears (*Coix lacryma-jobi*) oil; jojoba oil; kiwi (*Actinidia chinensis*) seed oil; kukui (*Aleurites moluccana*) nut oil; lard; linseed (*Linum usitatissiumum*) oil; lupin (*Lupinus albus*) oil; macadamia nut oil; *Macadamia ternifolia* seed oil; *Macadamia integrifolia* seed oil; maleated soybean oil; mango (*Mangifera indica*) seed oil; marmot oil; meadowfoam (*Limnanthes fragraalba*) seed oil; menhaden oil; milk lipids; mink oil; *Moringa pterygosperma* oil; *Mortierella* oil; musk rose (*Rosa moschata*) seed oil; neatsfoot oil; neem (*Melia azadirachta*) seed oil; oat (*Avena sativa*) kernel oil; olive (*Olea europaea*) husk oil; olive (*Olea europaea*) oil; omental lipids; orange roughy oil; ostrich oil; oxidized corn oil; palm (*Elaeis guineensis*) kernel oil; palm (*Elaeis guineensis*) oil; passionflower (*Passiflora edulis*) oil; peach (*Prunus persica*) kernel oil; peanut (*Arachis hypogaea*) oil; pecan (*Caiya illinoensis*) oil; pengawar djambi (*Cibotium barometz*) oil; pistachio (*Pistacia vera*) nut oil; placental lipids; poppy (*Papaver orientale*) oil; pumpkin (*Cucurbita pepo*) seed oil; quinoa (*Chenopodium quinoa*) oil; rapeseed (*Brassica campestris*) oil; rice (*Oryza sativa*) bran oil; rice (*Oryza sativa*) germ oil; safflower (*Carthamus tinctorius*) oil; salmon oil; sandalwood (*Santalum album*) seed oil; seabuchthorn (*Hippophae rhamnoides*) oil; sesame (*Sesamum indicum*) oil; shark liver oil; shea butter (*Butyrospermum parkii*); silk worm lipids; skin lipids; soybean (*Glycine soja*) oil; soybean lipid; Sphingolipids; sunflower (*Helianthus annuus*) seed oil; sweet almond (*Prunus amygdalus dulcis*) oil; sweet cherry (*Prunus avium*) pit oil; tali oil; tallow; tea tree (*Melaleuca alternifolia*) oil; telphairia pedata oil; tomato (*Solanum lycopersicum*) oil; *Trichodesma zeylanicum* oil; tuna oil; vegetable oil; walnut (*Juglans regia*) oil; wheat bran lipids; and wheat (*Triticum vulgare*) germ oil and mixtures thereof.

In certain embodiments, the oil is present in the compositions of the present invention in a total amount of from 0.01% (or about 0.01%) to 99.98% (or about 99.98%), or optionally 10% (or about 10%) to 90% (or about 90%), or optionally from 20% (or about 20%) to 70% (or about 70%), or optionally from 25% (or about 25%) to 50% (or about 50%), or optionally from 30% (or about 30%) to 40% (or about 40%), or optionally about 33%, by weight of the admixture.

In certain embodiments the oil mixture used as a source of the fatty acid mixture is formed from oils selected to provide the following fatty acid composition: 0.3% (or about 0.3%) myristic acid, 19% (or about 19%) palmitic acid, 0.5% (or about 0.5%) palmitoleic acid, 13% (or about 13%) stearic acid, 44.4% (or about 44.4%) oleic acid, 21.3% (or about 21.3%) linoleic acid, and 0.5% (or about 0.5%) linolenic acid. In certain embodiments the oil mixture used as a source of the fatty acid mixture is formed from oils selected from the group consisting of cocoa butter, olive oil, cottonseed oil and mixtures thereof.

In certain embodiments, the fatty acid mixture or source of the fatty acid mixture is present in the compositions of the present invention in an amount from 0.01% (or about 0.01%) to 99.98% (or about 99.98%), or optionally 10% (or about 10%) to 90% (or about 90%), or optionally from 20% (or about 20%) to 70% (or about 70%), or optionally from 25% (or about 25%) to 50% (or about 50%), or optionally from 30% (or about 30%) to 40% (or about 40%), or optionally about 33%, by weight of the admixture.

In certain embodiments, the ratio of the acid component to the fatty acid mixture component on a weight/weight basis is from 0.01:1 (or about 0.01:1) to 1:0.01 (or about 1:0.01), optionally from 1:1 (or about 1:1) to 1:0.1 (or about 1:0.1), optionally from 1:1 (or about 1:1) to 1:0.5 (or about 1:0.5), or optionally, 1:1 (or about 1:1).

In certain embodiments, the ratio of the fatty acid mixture component to the antioxidant component on a weight/weight basis is from 0.01:1 (or about 0.01:1) to 1:0.01 (or about 1:0.01), optionally from 1:1 (or about 1:1) to 1:0.1 (or about 1:0.1), optionally from 1:1 (or about 1:1) to 1:0.5 (or about 1:0.5).

In certain embodiments, the ratio of the pyruvic acid component or the fatty acid mixture component to the antioxidant component on a weight/weight basis is from 1:1 (or about 1:1) to 1:0.01 (or about 1:0.01).

Other Materials:

Various other materials may also be present in the compositions useful in the subject invention. These include humectants, proteins and polypeptides, preservatives, an alkaline agent and mixtures thereof. The compositions of the present invention may also comprise chelating agents (e.g., EDTA, citric acid, phytic acid) and preservatives (e.g., parabens). In addition, the topical compositions useful herein can contain conventional cosmetic adjuvants, such as dyes, sunscreen (e.g., titanium dioxide), pigments, and fragrances. A more detailed discussion of these and other materials can be found in previously incorporated U.S. Patent Publication 2008/0145331 to Bruning et al. as well as in U.S. Pat. No. 5,658,956 to Martin et al., which patent is herein incorporated by reference in its entirety.

Mixtures of the above preservatives can also be used.

In certain embodiments, the compositions of the present invention have an apparent pH of from 4.0 (or about 4.0) to 7.0 (or about 7.0), optionally from 4.0 (or about 4.0) to 6.0 (or about 6.0), optionally from 4.5 (or about 4.5) to 5.5 (or about 5.5). In certain rinse off or wash off embodiments, the compositions of the present invention have an apparent pH of from 3.0 (or about 3.0) to 8.0 (or about 8.0), optionally from 4.0 (or about 4.0) to 6.0 (or about 6.0), Methods of Use The use of compositions of this invention for accelerating the onset of the anagen phase of hair growth in a mammal and/or increasing the rate at which terminal hair appears on the skin by topical application of the present compositions was determined by the mice studies described below.

In certain embodiments, the compositions of this invention should be applied topically to the desired area of the mammalian or human body at least once per day for at least 11 weeks, optionally at least 9 weeks, or optionally at least 7 weeks. The hair growth benefits of the present invention may be maintained indefinitely by chronic administration of the compositions of the present invention.

EXAMPLES

The compositions of the present invention as described in following examples illustrate specific embodiments of compositions of the present invention, but are not intended to be limiting thereof. Other modifications can be undertaken by the skilled artisan without departing from the spirit and scope of this invention.

Example 1

Treatment formulation #1 (Table 1) is prepared as described below using conventional mixing technology.

TABLE 1

| Treatment formulation # 1 | |
|---|---|
| Ingredient | Inventive Treatment Formulation # 1 % (wt/wt) |
| Ethanol | 20.00 |
| Pentylene glycol[1] | 4.00 |
| Glycerin | 12.00 |
| Lactic acid | 3.20 |

TABLE 1-continued

| Treatment formulation # 1 | |
|---|---|
| Ingredient | Inventive Treatment Formulation # 1 % (wt/wt) |
| Minoxidil | 5.07 |
| Butylated hydroxytoluene (BHT) | 0.10 |
| Water | 45.13 |
| Cetyl lactate[4] | 3.00 |
| Sodium Pyruvate | 1.00 |
| Tocopheryl Acetate | 0.50 |
| Steareth-10[3] | 1.50 |
| Steareth-2[3] | 2.00 |
| Polyquaternium 37[2] | 1.50 |
| Total | 100.00 |
| Apparent pH | 4.6 |
| Viscosity[5] | 9500 cps |

[1]Hydrolite 5 supplied by Symrise, Teterboro, NJ
[2]Cosmedia Ultra 300 supplied by BASF, Florham Park, NJ
[3]supplied by Croda, Edison, NJ
[4]supplied by Ashland Inc., Covington, KY
[5]measured using a Brookfield RV (spindle 4, speed 6 RPM at 1 minute following the temperature equilibrated at 25° C. ± 1° C.)

The Treatment formulation #1 is prepared according to the following procedure:

(1) The ethanol is added to a suitably sized first beaker equipped with an overhead mixer.

(2) The pentylene glycol, glycerin, citric acid (if applicable) and lactic acid are added to the beaker and the mixture is mixed for about 2 minutes.

(3) The minoxidil and BHT are added to the beaker and is stirred for about 10 minutes or until dissolved.

(4) The water is added slowly and the mixture is mixed for about 2 minutes.

(5) In a separate second beaker equipped with a hotplate and magnetic stirrer, steareth-10, steareth-2, cetyl lactate and tocopheral acetate are premixed to form an oil phase.

(6) The premix heated to about 60° C. and is stirred with the magnetic stirring bar until dissolved or melted and oil phase is uniform.

(7) The premix is added with stirring to the minoxidil containing water phase in the first beaker and is mixed for about 5 minutes.

(8) The sodium pyruvate is added to the first beaker and is mixed for about 3 minutes.

(9) The Polyquaternium 37 is added to the first beaker and the mixture in the first beaker is homogenized at 7,000 rpm using a Silverson L4RT homogenizer (Silverson, Birmingham, UK) for about 5 minutes.

Example 2

In vitro skin permeation of 5% minoxidil compositions through human cadaver skin.

A skin penetration study evaluated the penetration of minoxidil into different skin layers for the Inventive Treatment Formulation #1 of Example 1 vs. a commercially available Walgreen's 5% Minoxidil Topical Solution was used as Comparative Treatment Formulation #2. The pH of the Walgreen's 5% Minoxidil Topical Solution was measured to be 8.1.

A well-known Franz diffusion cell method (as taught in US20020006418 A1, which publication is hereby incorporated by reference) was used. Franz cells had a diameter of 0.5 cm² and a volume of liquid receptor of 5 ml. A magnetic stirrer bar was added in the donor compartment. The liquid receptor was filled with Phosphate-buffered saline (PBS) solution. Air bubbles in the donor compartment were removed. The system was thermostated at 37° C. above a magnetic stirrer to ensure the homogeneity of the liquid receptor during the experiment. A cadaver skin sample from a commercial tissue bank (Ohio Valley Tissue and Skin Center, Cincinnati, Ohio, dermatomed to approximately 0.4 mm) was cut to fit the glass diffusion cell and mounted skin on the Franz cell. A test sample of 20 microliters was applied on the skin surface. Samples were collected from the receptor compartment at scheduled time points of 0, 1, 3 and 6 hours.

At the end of the study the skin surface was washed with a cotton swab of liquid receptor (PBS). After washing, skin extraction was performed either on full skin or on separated skin layers of epidermis and dermis. Samples collected from the receptor compartment and from the skin extraction were analyzed for minoxidil levels with a Waters High-performance liquid chromatography (HPLC) system with the procedure listed below. The results are shown in Table 2. The final average minoxidil levels in different skin layers are reported in micrograms (μg) for 3 different replicates. A minoxidil mass balance study was also conducted and the % of recovery of minoxidil was better than 95% for both the control and the inventive formulation.

HPLC Procedure for Minoxidil Quantification

A HPLC System (Waters Alliance® HPLC system) was used to measure minoxidil with UV absorption response at 286 nm. A Luna 5 μM C18(2) 250×4.6-mm HPLC column (Phenomenex) was used to separate the minoxidil analyte from other impurities in the extract samples for surface rinse, stripped tape, epidermis, dermis, and receptor solution. The mobile phase was an isocratic 80% (70:29:1 water/methanol/acetic acid—pH 3.3): 20% methanol.

TABLE 2

| | Time (hr) | Comparative Treatment Formulation #2 (microgram) | Inventive Treatment Formulation #1 (microgram) | Ratio of Inventive Treatment Formulation #1 to Comparative Treatment Formulation #2 |
|---|---|---|---|---|
| Cumulative Minoxidil in Receptor | 3 | 25.6 | 24.72132 | 0.97 |
| | 6 | 53.1 | 74.66605 | 1.40 |
| | 24 | 142. | 380.7399 | 2.68 |
| Dermis | 24 | 15.4 | 64.68762 | 4.21 |
| Epidermis | 24 | 119.7 | 203.5053 | 1.70 |
| Tapes | 24 | 64.7 | 19.93 | 0.31 |
| % Recovered | | 95.5 | 95.3 | |

Because the target tissue for topical minoxidil delivery is the hair follicles (or hair "roots") residing deep in the dermis, only minoxidil that penetrated into and cross the dermis layer could reach the hair follicles, and therefore, is of practical significance. The cetyl lactate (or a $C_8$-$C_{24}$ alcohol ester of a carboxylic acid) containing Inventive Treatment Formulation #1 provided significantly enhanced minoxidil delivery deeper into the human skin versus Comparative Treatment Formulation #2 (i.e., by about 400% into the dermis which is where the hair bulb is located), especially in skin tissues, as demonstrated by the results in Table 2. Moreover, Inventive Treatment Formulation #1 provided above described higher penetration despite Comparative Treatment Formulation #2 containing signficant amounts of two well known skin permeation enhancers, namely ethanol (30%) and propylene glycol (50%). (See Williams AC1, Barry B W, "Penetration enhancers" Adv Drug Deliv Rev. 2004 Mar. 27; 56(5):603-18. The Inventive Treatment Formulation #1, by contrast, contains only 20% of ethanol and 4% glycol.

Example 3

A mice hair growth study was performed using the hair growth compositions of the present invention as detailed below.

Procedure:

In vivo hair growth study was conducted in a mouse model similar to that described in U.S. Pat. No. 6,419,913 B1, which patent is hereby incorporated by reference. Five female mice (C3H mice, Charles River Breeding Laboratories, Kingston, N.Y.) were included for each test article (i.e., inventive and comparative test formulations of Examples 1 and 2).

To determine the acceleration in the onset of the anagen phase in the C3H mice, C3H female mice at 6-7 weeks of age were purchased from Taconic Farms (Germantown, N.Y.). C3H mice's hair growth cycles have similar anagen, catagen and telogen phases. (Miyamoto I.; Hamada K., Journal of Dermatological Science, Volume 10, Number 1, July 1995, pp. 99-99 (1)). The hair growth cycles are shown on Table 3.

TABLE 3

| Weeks after Birth | Hair Growth Stage |
|---|---|
| Week 0 | Morphogenesis |
| Week 2 | Catagen |
| Week 3 | Telogen |
| Week 4 | Anagen |
| Week 6 | Catagen |
| Week 7 | Telogen |
| Week 15 | Anagen |

Each phase is shorter than its corresponding phase in humans and synchronized. This makes C3H mice a useful model for studying the induction activity of hair re-growth by active substances. C3H mice have a long telogen window from week 7 to week 15. Therefore, hair regrowth studies typically start at week 7 and end at week 15, i.e. the duration of a study is about 8 weeks.

Mice were housed in appropriately sized cages in an environmentally controlled room with a 12-hour light-12-hour dark photoperiod and supplied with food and water ad libitum. Animal care was based on the "Guide for the Care and Use of Laboratory Animals", NIH Publication No. 85-23. Once all mice entered their prolonged telogen/resting phase of the hair cycle, they were clipped over the dorsal area about 1.5×5 cm (Wahl Clippers 8900 Series, Blade #1086). Five female mice per group were clipped while sedated with 2% induction and maintenance isoflurane and 0.5 L Oxygen. The actual number of mice represented in the data may vary due to inadvertent death of one or more mice during study.

Determination of Accelerated Onset of Anagen Phase

The mice were shaved with a short hair clipper to hairless on their back as determined by visual inspection (2×5 $cm^2$ area) at the start of the study. Test articles were prepared as described above. The test articles were applied daily to the shaved areas of the mice daily at 0.2 ml per dose. Both the hair anagen phase and the hair coverage were observed by visual inspection and recorded 5 days a week for each mouse's hair condition (Telogen phase: resting phase in hair growth cycle—shaved skin shown no dark hair bulbs/roots; Anagen phase: anagen follicles, i.e. follicles in the growth state of the hair growth cycle—shaved skin shows dark hair bulbs/roots) A study log (or, Anagen Phase Log) documenting day-to-day observations of mice entering anagen (grey skin, the first visual clue to a new hair growth) were recorded. Treatments continued for 8 weeks.

The treatment groups and treatment formulations were selected as follows:

| Group | Treatment Formulation |
|---|---|
| A | Untreated |
| B | Comparative Treatment Formulation # 2 as described in Example 2 |
| C | Inventive Treatment Formulation # 1 of Example 1 |

As shown in Table 4 below, the Inventive Treatment Formulation #1 resulted in hair follicles turning from resting state (telogen phase) to growth state (anagen phase) in about four days faster than the Comparative Treatment Formulation #2.

TABLE 4

Anagen Phase Onset Log

| Duration after treatment | Untreated | Comparative Treatment Formulation # 2 as described in Example 2 | Inventive Treatment Formulation # 1 of Example 1 |
|---|---|---|---|
| Day 1 | Telogen | Telogen | Telogen |
| Day 2 | Telogen | Telogen | Anagen |
| Day 3 | Telogen | Telogen | Anagen |
| Day 6 | Telogen | Anagen | Anagen |
| Week 2 | Telogen | Anagen | Anagen |
| Week 3 | Telogen | Anagen | Anagen |
| Week 4 | Telogen | Anagen | Anagen |
| Week 5 | Telogen | Anagen | Anagen |
| Week 6 | Telogen | Anagen | Anagen |

Table 5 shows anagen phase onsets for Untreated, Comparative Treatment Formulation #2 and Inventive Treatment Formulation #1 as recorded in the anagen phase log.

TABLE 5

Anagen Phase Onset

| Group | Treatment Formulation | Anagen Phase Onset (Days after Treatment) |
|---|---|---|
| A | Untreated | 41 |
| B | Comparative Treatment Formulation # 2 as described in Example 2 | 6 |
| C | Inventive Treatment Formulation # 1 | 2 |

The data in Table 5 demonstrates that the onset of anagen phase occurred 4 days earlier in Group C (Test Formula 2) than in the Group B (Test Formula 1). Group C is 39 days earlier than in Group A of untreated.

The average degree of terminal hair coverage across mice in each Group was determined by visual inspection of the images taken weekly. A hair coverage index was used in documenting the mice hair growth stages. The phrase "degree of terminal hair coverage", means the observed average estimated percentage of the treated site which is covered by terminal hair.

The phrase "faster degree of terminal hair coverage" means that a degree of terminal hair coverage is achieved faster in time. The term "average" means the average across the mice in each group. The term "observed" or "visual observations" means visual inspection.

The groups were then ranked in order of highest degree of terminal hair coverage to lowest degree of terminal hair coverage according to the following hair coverage scoring system.

Hair Coverage Scoring System

| Grading | Description |
|---|---|
| 0 | No hair at all |
| 1 | A few patches of hair growth, less than ¼ of the dorsal area |
| 2 | Hair growth covering about ¼ of the dorsal area |
| 3 | Hair growth covering about ½ of the dorsal area |
| 4 | Hair growth covering more than ¾ of the dorsal area |
| 5 | Hair growth completely covering treatment area |

Table 6 is a ranking of the degree of terminal hair coverage for Test Formulation 1, Test formula 2 and Untreated, based on images taken at different time points.

Visual observation of images taken at week 0 (day that mice were shaved) demonstrated that, at this stage of the study, all the mice of test groups had all terminal hair removed.

TABLE 6

Hair Coverage Score Table for Mice Shaved Hair (n = 5 per cell at the study start)

| | Untreated | | Comparative Treatment Formulation # 2 as described in Example 2 | | Inventive Treatment Formulation # 1 | |
|---|---|---|---|---|---|---|
| Weeks | Individual Score | Average Score | Individual Score (per mouse) | Average Score | Individual Score (per mouse) | Average Score |
| 1 | 0, 0, 0 | 0 | 0 | 0 | 1, 1, 1, 1, 1 | 1 |
| 2 | 0, 0, 0 | 0 | 1, 1, 1, 1, 1 | 1 | 2, 2, 2, 2, 2 | 2 |
| 3 | 0, 0, 0 | 0 | 1, 1, 1, 1, 1 | 1 | 3, 3, 3, 3, 3 | 3 |
| 4 | 0, 0, 0 | 0 | 1, 1, 1, 1, 1 | 1 | 5, 5, 5, 5, 5 | 5 |
| 5 | 0, 0, | 0 | 1, 1, 1, 1, 1 | 1 | 5, 5, 5, 5, 5 | 5 |
| 6 | 0, 0, 0 | 0 | 1, 2, 3* | 2 | 5, 5, 5, 5, 5 | 5 |
| 7 | 1, 1, 1 | 1 | 1, 4, 4* | 3 | 5, 5, 5, 5, 5 | 5 |

*Two test mice were sacrificed after Week 5 evaluation for tissue histology

The ranking in Table 6 demonstrates that mice skin treated with Inventive Treatment Formulation #1 containing the $C_8$-$C_{24}$ alcohol ester of a carboxylic acid (i.e., cetyl lactate), demonstrated a much faster degree of terminal hair coverage than the Comparative Treatment Formulation #2.

Example 4

Compositions (e.g., oil in water emulsion) or gels incorporating the hair growth composition of the present invention were prepared using conventional mixing technology and are illustrated as Comparative Formulation A (without the $C_8$-$C_{24}$ alcohol ester of a carboxylic acid) and Inventive Treatment Formulation B (with the $C_8$-$C_{24}$ alcohol ester of a carboxylic acid) in Table 7.

TABLE 7

| Chemical Name | Comparative Formulation A % (w/w) | Inventive Treatment Formulation B % (w/w) |
|---|---|---|
| Ethyl Alcohol | 21.00 | 21.00 |
| Pentylene Glycol | 4.00 | 4.00 |
| Glycerin | 12.00 | 12.00 |
| Citric Acid | 0.20 | 0.20 |
| Lactic Acid | 3.00 | 3.00 |
| Minoxidil | 5.07 | 5.07 |
| Butylated Hydroxytoluene | 0.10 | 0.10 |
| Steareth-10 | 1.50 | 1.50 |
| Cetyl lactate | n/a | 1.50 |
| Water | 50.63 | 49.13 |
| Polyquaternium-37 | 2.50 | 2.50 |
| pH = 4.50 | 100.00 | 100.00 |

Comparative Formulation A and Inventive Treatment Formulation B were prepared according to the following procedure:
(1) The ethyl alcohol is added to a suitably sized first glass container with an overhead mixer.
(2) The pentylene glycol, glycerin, citric acid, & lactic acid are added to the container and the mixture is mixed for about 2 minutes.
(3) The minoxidil, and BHT are added to the beaker and is stirred for about 10 minutes or until dissolved.
(4) The water is added slowly and the mixture is mixed for about 2 minutes.
(5) In a separate second beaker equipped with a hotplate and magnetic stirrer, the steareth-10, and cetyl lactate acetate are premixed.
(6) The premix heated to about 60° C. and is stirred with the magnetic stirring bar until completely melted and a uniform oil phase is formed.
(7) The premix is added with stirring to the minoxidil containing water phase in the first container and is mixed for about 5 minutes.
(9) The Polyquaternium 37 is added to the first container and the mixture in the first container is homogenized at 7,000 rpm using a Silverson L4RT homogenizer (Silverson, Birmingham, UK) for about 5 minutes.

Example 5

In Vitro skin permeation of 5% minoxidil compositions through human cadaver skin.
The skin penetration study as described in Example 2 was used to evaluate the penetration of minoxidil into different skin layers for the Inventive Treatment Formulation B vs. Comparative Formulation A.
A cadaver skin sample from a commercial tissue bank (Allosource, Centenia, Colo., dermatomed to approximately 0.4 mm) was cut to fit the glass diffusion cell and mounted skin on the Franz cell. A test sample of 20 microliters was applied on the skin surface. Samples were collected from the receptor compartment at scheduled time points of 0, 2, 4 and 6 hours.
At the end of the study the skin surface was washed with a cotton swab of liquid receptor (PBS). After washing, skin extraction was performed either on full skin or on separated skin layers of epidermis and dermis. Samples collected from the receptor compartment and from the skin extraction were analyzed for minoxidil levels with a Waters High-performance liquid chromatography (HPLC) system with the procedure listed below. The results are shown in Table 8.

The final average minoxidil levels in different skin layers are reported in micrograms (μg) for 3 different replicates. A minoxidil mass balance study was also conducted and the % of recovery of minoxidil was better than 95% for both the control and the inventive formulation.

HPLC Procedure for Minoxidil Quantification

A HPLC System (Waters Alliance® HPLC system) was used to measure minoxidil with UV absorption response at 286 nm. A Luna 5 μM C18(2) 250×4.6-mm HPLC column (Phenomenex) was used to separate the minoxidil analyte from other impurities in the extract samples for surface rinse, stripped tape, skin (epidermis/dermis), and receptor solution. The mobile phase was an isocratic 80% (70:29:1 water/methanol/acetic acid—pH 3.3): 20% methanol.

TABLE 8

| | Time (hr) | Comparative Treatment Formulation A (microgram) | Inventive Treatment Formulation B (microgram) | Ratio of Inventive Treatment Formulation B to Comparative Treatment Formulation A |
|---|---|---|---|---|
| Cumulative Minoxidil in Receptor | 2 | 58.6 | 56.4 | 0.96 |
| | 4 | 128.8 | 117.1 | 0.91 |
| | 6 | 185.1 | 173.5 | 0.94 |
| Skin (Dermal + Epi-dermis) | 6 | 67.4 | 138.5 | 2.06 |
| Tapes | 6 | 24.4 | 56.2 | 2.31 |
| % Recovered | | 95.5 | 95.3 | |

Because the target tissue for topical minoxidil delivery is the hair follicles (or hair "roots") residing deep in the dermis, only minoxidil that penetrated into and cross the skin layer could reach the hair follicles, and therefore, is of practical significance. The cetyl lactate (or $C_8$-$C_{24}$ alcohol ester of a carboxylic acid) containing Inventive Treatment Formulation B provided significantly enhanced minoxidil delivery deeper into the human skin versus Comparative Formulation A (i.e., by about 206% into the skin tissues) as demonstrated by the results in Table 8.

Example 6

Compositions for Comparative Formulation X (without the $C_8$-$C_{24}$ alcohol ester of a carboxylic acid) and Inventive Formulation Y (with the $C_8$-$C_{24}$ alcohol ester of a carboxylic acid)

Compositions incorporating the composition of the present invention can be prepared using conventional mixing technology and are illustrated as Comparative Example X and Inventive Example Y in Table 9.

TABLE 9

| Chemical Name | Comparative Formulation X Composition % (w/w) | Inventive Formulation Y Composition % (w/w) |
|---|---|---|
| Ethyl Alcohol | 21.00 | 21.00 |
| Pentylene Glycol | 4.00 | 4.00 |
| Glycerin | 12.00 | 12.00 |
| Citric Acid | 0.20 | 0.20 |
| Lactic Acid | 3.00 | 3.00 |

TABLE 9-continued

| Chemical Name | Comparative Formulation X Composition % (w/w) | Inventive Formulation Y Composition % (w/w) |
|---|---|---|
| Minoxidil | 5.00 | 5.00 |
| Butylated Hydroxytoluene | 0.10 | 0.10 |
| Water | 52.70 | 49.70 |
| Polyquaternium-37 | 2.00 | 2.00 |
| Cetyl Lactate | N/A | 3.00 |
| Total | 100.00 | 100.00 |

Comparative Formulation X and Inventive Formulation Y were prepared according to the following procedure:
(1) The ethyl alcohol is added to a suitably sized glass container with an overhead mixer.
(2) The pentylene glycol, glycerin, citric acid, & lactic acid are added to the container in the step (1) and the mixture is mixed for about 2 minutes.
(3) The minoxidil, and BHT are added to the container and is stirred for about 10 minutes or until completely dissolved. For Comparative Formula, skip the process (5) and (6).
(4) Water is added to the above mixing container. Following with Polyquaternium-37 added slowly to the mixing container and mixed until completely dissolved.
(5) In a separate second glass container equipped with a hotplate and magnetic stirrer, the premix of cetyl lactate is weighed in and heated to about 45° C. and is stirred with a magnetic stirring bar until completely melted.
(6) The premix is added with stirring to the minoxidil containing aqueous phase in the first container and is mixed for about 5 minutes.

Example 7

In vitro skin permeation of 5% minoxidil compositions through human cadaver skin.

A skin penetration study evaluated the penetration of minoxidil into different skin layers for the Comparative Formulation X and Inventive Formulation Y.

The skin penetration study as described in Example 2 was used to evaluate the penetration of minoxidil into different skin layers for the Comparative Formulation X and Inventive Formulation Y.

A cadaver skin sample from a commercial tissue bank (Allosource, Centenia, Colo., dermatomed to approximately 0.4 mm) was cut to fit the glass diffusion cell and mounted skin on the Franz cell. A test sample of 20 microliters was applied on the skin surface. Samples were collected from the receptor compartment at scheduled time points of 0, 6 and 24 hours.

At the end of the study the skin surface was washed with a cotton swab of liquid receptor (PBS). After washing, skin extraction was performed either on full skin or on separated skin layers of epidermis and dermis. Samples collected from the receptor compartment and from the skin extraction were analyzed for minoxidil levels with a Waters high-performance liquid chromatography (HPLC) system with the procedure listed below. The results are shown in Table 10. The final average minoxidil levels in different skin layers are reported in micrograms (μg) for 3 different replicates. A minoxidil mass balance study was also conducted and the % of recovery of minoxidil was better than 92.5% for both the comparative and the inventive formulation.

HPLC Procedure for Minoxidil Quantification

A HPLC System (Waters Alliance® HPLC system) was used to measure minoxidil with UV absorption response at 286 nm. A Luna 5 μM C18(2) 250×4.6-mm HPLC column (Phenomenex) was used to separate the minoxidil analyte from other impurities in the extract samples for surface rinse, stripped tape, epidermis, dermis, and receptor solution. The mobile phase was an isocratic 80% (70:29:1 water/methanol/acetic acid—pH 3.3): 20% methanol.

TABLE 10

| | Time (hr) | Comparative Formulation X (microgram) | Inventive Formulation Y (microgram) | Ratio of Inventive Formulation Y to Comparative Formulation X |
|---|---|---|---|---|
| Cumulative Minoxidil in Receptor | 0.00 | 0 | 0 | n/a |
| | 6.00 | 1000 | 1149 | 1.1 |
| | 24.00 | 2423 | 2851 | 1.2 |
| Dermal | 24.00 | 16 | 77 | 4.7 |
| Epidermis + Tape | 24.00 | 49 | 236 | 4.8 |
| % Recovered | | 92.5 | 97.5 | |

Because the target tissue for topical minoxidil delivery is the hair follicles (or hair "roots") residing deep in the dermis, only that portion of minoxidil penetrating into and crossing the skin layer could reach the hair follicles is, therefore, of practical significance. The cetyl lactate (or $C_8$-$C_{24}$ alcohol ester of a carboxylic acid) containing Inventive Formulation Y provided significantly enhanced minoxidil delivery deep into the human skin versus Comparative Formulation X (i.e. by about 470% into the dermis), as demonstrated by the results in Table 10.

Example 8

A composition incorporating the composition of the present invention can be prepared using conventional mixing technology and is illustrated in Table 11.

TABLE 11

| Chemical Name | Theoretical % (w/w) |
|---|---|
| Ethyl Alcohol | 53.50 |
| Glycerin | 3.00 |
| Citric Acid | 0.20 |
| Lactic Acid | 1.20 |
| Minoxidil | 5.00 |
| Butylated Hydroxytoluene | 0.10 |
| Water | 31.50 |
| Hydroxyethylcellulose | 1.00 |
| Cetyl Lactate | 3.0 |
| pH = 5.69 | 100.00 |

Example 9

Comparative Treatment formulation A" and Inventive Treatment formulation B" (Table 15) are prepared as described below using conventional mixing technology.

TABLE 12

| Ingredient | Comparative Treatment Formulation A" % (wt/wt) | Inventive Treatment Formulation B" % (wt/wt) |
|---|---|---|
| Ethanol | 21.00 | 21.00 |
| Pentylene glycol[1] | 4.00 | 4.00 |
| Glycerin | 12.00 | 12.00 |
| Citric acid | 0.20 | 0.20 |
| Lactic acid | 3.00 | 3.00 |
| Minoxidil | 5.00 | 5.00 |
| Butylated hydroxytoluene (BHT) | 0.10 | 0.10 |
| Water | 43.71 | 40.71 |
| Cetyl Lactate | n/a | 3.00 |
| Sodium Pyruvate | 1.0 | 1.00 |
| Tocopheryl Acetate | 0.50 | 0.50 |
| Steareth-10 | 1.50 | 1.50 |
| Steareth -2 | 2.00 | 2.00 |
| Cotton seed oil | 1.33 | 1.33 |
| Cocoa butter oil | 1.33 | 1.33 |
| Olive oil | 1.33 | 1.33 |
| Polyquaternium 37 | 2.00 | 2.00 |
| Total | 100.00 | 100.00 |
| Apparent pH | 4.6 | 4.6 |

[1]Hydrolite 5 supplied by (Symrise, Teterboro, NJ)
[2]Cosmedia Ultra 300 supplied by (BASF, Florham Park, N.J)

Comparative Treatment Formulation A" and Inventive Treatment Formulation B" are prepared according to the following procedure:

(1) The ethanol is added to a suitably sized first beaker with an overhead mixer.
(2) The pentylene glycol, glycerin, citric acid, & lactic acid, minoxidil, and BHT are added to the beaker and the mixture is mixed for about 10 minutes or until dissolved.
(3) The water is added slowly and the mixture is mixed for about 2 minutes.
(4) In a separate second beaker equipped with a hotplate and magnetic stirrer, the steareth-10, steareth-2, tocopheral acetate, vegetable oils and or cetyl lactate are premixed to form an oil phase with a heating to about 60° C. and is stirred with the magnetic stirring bar until dissolved or melted and oil phase is uniform.
(5) The premix is added with stirring to the minoxidil containing water phase in the first beaker and is mixed for about 5 minutes.
(6) The sodium pyruvate is added to the first beaker and is mixed for about 3 minutes.
(7) The Polyquaternium 37 is added to the first beaker and the mixture in the first beaker is homogenized at 7,000 rpm using a Silverson L4RT homogenizer (Silverson, Birmingham, UK) for about 5 minutes.

Example 10

In vitro skin permeation of 5% minoxidil compositions through human cadaver skin.

The skin penetration study as described in Example 5 was used to evaluate the penetration of minoxidil into different skin layers for the Inventive Treatment Formulation B" vs. Comparative Formulation A".

A cadaver skin sample from a commercial tissue bank (Allosource, Centenia, Colo., dermatomed to approximately 0.4 mm) was cut to fit the glass diffusion cell and mounted skin on the Franz cell. A test sample of 20 microliters was applied on the skin surface. Samples were collected from the receptor compartment at scheduled time points of 6 and 24 hours.

At the end of the study the skin surface was washed with a cotton swab of liquid receptor (PBS). After washing, skin extraction was performed either on full skin or on separated skin layers of epidermis and dermis. Samples collected from the receptor compartment and from the skin extraction were analyzed for minoxidil levels with a Waters High-performance liquid chromatography (HPLC) system with the procedure listed below. The results are shown in Table 13. The final average minoxidil levels in different skin layers are reported in micrograms (μg) for 3 different replicates. A minoxidil mass balance study was also conducted and the % of recovery of minoxidil was better than 95% for both the control and the inventive formulation.

HPLC Procedure for Minoxidil Quantification

A HPLC System (Waters Alliance® HPLC system) was used to measure minoxidil with UV absorption response at 286 nm. A Luna 5 μM C18(2) 250×4.6-mm HPLC column (Phenomenex) was used to separate the minoxidil analyte from other impurities in the extract samples for surface rinse, stripped tape/epidermis, dermis, and receptor solution. The mobile phase was an isocratic 80% (70:29:1 water/methanol/acetic acid—pH 3.3): 20% methanol.

TABLE 13

| Location | Time (hr) | Comparative Treatment Formulation A" (microgram) | Inventive Treatment Formulation B" (microgram) | Ratio of Inventive Treatment Formulation B" to Comparative Treatment Formulation A" |
|---|---|---|---|---|
| Cumulative Minoxidil Receptor | 6 | 12 | 53.2 | 4.4 |
|  | 24 | 23 | 95 | 4.1 |
| Dermis | 24 | 50.1 | 75 | 1.5 |
| Epi + Tape | 24 | 200 | 235 | 1.2 |

Because the target tissue for topical minoxidil delivery is the hair follicles (or hair "roots") residing deep in the dermis, only minoxidil that penetrated into and cross the skin layer could reach the hair follicles, and therefore, is of practical significance. The cetyl lactate (or $C_8$-$C_{24}$ alcohol ester of a carboxylic acid) containing Inventive Treatment Formulation B" provided significantly enhanced minoxidil delivery deep into the human skin versus Comparative Treatment Formulation A" (i.e. by about 150% into the dermis, as demonstrated by the results in Table 13.

Example 11

A composition incorporating the composition of the present invention can be prepared using conventional mixing technology and is illustrated in Table 14.

TABLE 14

| Ingredient | Formulation % (wt/wt) |
|---|---|
| Ethanol | 20.00 |
| Pentylene glycol[1] | 4.00 |
| Glycerin | 12.00 |
| Lactic acid | 3.20 |
| Minoxidil | 5.07 |
| Butylated hydroxytoluene (BHT) | 0.10 |
| Water | 49.36 |
| Cocoa Butter NF | 1.33 |
| Olive Oil NF | 1.33 |
| Cottonseed Oil NF | 1.33 |

TABLE 14-continued

| Ingredient | Formulation % (wt/wt) |
|---|---|
| Cetyl Lactate[4] | 2.00 |
| Sodium Pyruvate | 1.0 |
| Tocopheryl Acetate | 0.5 |
| Stearech-2[3] | 1.00 |
| Polyquaternium 37[2] | 2.5 |
| Total | 100.00 |

[1]Hydrolite 5 supplied by Symrise, Teterboro, NJ
[2]Cosmedia Ultra 300 supplied by BASF, Florham Park, N.J.
[3]supplied by Croda, Edison, NJ
[4]supplied by Ashland Inc., Covington, KY The above formulation is prepared according to the following procedure:

(1) The ethanol is added to a suitably sized first beaker with an overhead mixer.
(2) The pentylene glycol, glycerin, and lactic acid are added to the beaker and the mixture is mixed for about 2 minutes.
(3) The minoxidil and BHT are added to the beaker and is stirred for about 10 minutes or until dissolved.
(4) The water is added slowly and the mixture is mixed for about 2 minutes.
(5) In a separate second beaker equipped with a hotplate and magnetic stirrer, the stearech-2, cetyl lactate and tocopheral acetate are premixed to form an oil phase.
(6) The premix heated to about 60° C. and is stirred with the magnetic stirring bar until dissolved or melted and oil phase is uniform.
(7) The premix is added with stirring to the minoxidil containing water phase in the first beaker and is mixed for about 5 minutes.
(8) The sodium pyruvate is added to the first beaker and is mixed for about 3 minutes.
(9) The Polyquaternium 37 is added to the first beaker and the mixture in the first beaker is homogenized at 7,000 rpm using a Silverson L4RT homogenizer (Silverson, Birmingham, UK) for about 5 minutes.

Example 12

Comparative Treatment formulation P and Inventive Treatment formulation Q (Table 15) are prepared as described below using conventional mixing technology.

TABLE 15

| Ingredient | Comparative Treatment Formulation P % (wt/wt) | Inventive Treatment Formulation Q % (wt/wt) |
|---|---|---|
| Ethanol | 20.00 | 20.00 |
| Pentylene glycol[1] | 4.00 | 4.00 |
| Glycerin | 12.00 | 12.00 |
| Lactic acid | 3.20 | 3.20 |
| Minoxidil | 5.07 | 5.07 |
| Butylated hydroxytoluene (BHT) | 0.10 | 0.10 |
| Water | 48.63 | 45.14 |
| Cetyl Lactate[4] | n/a | 3.00 |
| Sodium Pyruvate | 1.0- | 1.00 |
| Tocopheryl Acetate | 0.5- | 0.50 |
| Steareth-10[3] | 3.0 | 1.50 |
| Steareth-2[3] | n/a | 2.00 |
| Polyquaternium 37[2] | 2.5 | 2.50 |
| Total | 100.00 | 100.00 |
| Apparent pH | 4.6 | 4.6 |

[1]Hydrolite 5 supplied by Symrise, Teterboro, NJ
[2]Cosmedia Ultra 300 supplied by BASF, Florham Park, N.J.
[3]supplied by Croda, Edison, NJ
[4]supplied by Ashland Inc., Covington, KY The formulations P and Q are prepared according to the following procedure:

(1) The ethanol is added to a suitably sized first beaker with an overhead mixer.
(2) The pentylene glycol, glycerin, citric acid (if applicable) and lactic acid are added to the beaker and the mixture is mixed for about 2 minutes.
(3) The minoxidil and BHT are added to the beaker and is stirred for about 10 minutes or until dissolved.
(4) The water is added slowly and the mixture is mixed for about 2 minutes.
(5) In a separate second beaker equipped with a hotplate and magnetic stirrer, steareth-10, steareth-2 (if applicable), cetyl lactate (if applicable) and tocopheral acetate are premixed to form an oil phase.
(6) The premix heated to about 60° C. and is stirred with the magnetic stirring bar until dissolved or melted and oil phase is uniform.
(7) The premix is added with stirring to the minoxidil containing water phase in the first beaker and is mixed for about 5 minutes.
(8) The sodium pyruvate is added to the first beaker and is mixed for about 3 minutes.
(9) The Polyquaternium 37 is added to the first beaker and the mixture in the first beaker is homogenized at 7,000 rpm using a Silverson L4RT homogenizer (Silverson, Birmingham, UK) for about 5 minutes.

Example 13

In vitro skin permeation of 5% minoxidil compositions through human cadaver skin.

The skin penetration study as described in Example 10 was used to evaluate the penetration of minoxidil into different skin layers for the Inventive Treatment Formulation Q of Example 12 vs. a commercially available Walgreen's 5% Minoxidil Topical Solution which was used as Comparative Treatment Formulation R. The apparent pH of the Walgreen's 5% Minoxidil Topical Solution was measured to be 8.1. A separate study, as described in Example 10, compared the the penetration of minoxidil into different skin layers for the Comparative Treatment Formulation P of Example 12 vs. the commercially available Walgreen's 5% Minoxidil Topical Solution (Comparative Treatment Formulation R).

A cadaver skin sample from a commercial tissue bank (Allosourec, Centennial, Colo., dermatomed to approximately 0.4 mm) was cut to fit the glass diffusion cell and mounted skin on the Franz cell. A test sample of 20 microliters was applied on the skin surface. Samples were collected from the receptor compartment at scheduled time points of 0, 3, 6 and 24 hours.

At the end of the study the skin surface was washed with a cotton swab of liquid receptor (PBS). After washing, skin extraction was performed either on full skin or on separated skin layers of epidermis and dermis. Samples collected from the receptor compartment and from the skin extraction were analyzed for minoxidil levels with a Waters High-performance liquid chromatography (HPLC) system with the procedure listed below.

As noted above, the test was performed, comparing Inventive Treatment Formulation Q versus the Comparative Treatment Formulation R and, the test was performed again, using a different cadaver from the same skin commercial tissue bank—(Allosourec, Centennial, Colo., dermatomed to approximately 0.4 mm)—to compare Comparative Treatment Formulation P versus the Comparative Treatment Formulation R. A comparison of Inventive Treatment Formulation Q versus the Comparative Treatment Formulation P is extrapolated from the results of the described tests.

The results of the tests and the extrapolation comparison are shown in Tables 16 and 17. The final average minoxidil levels in different skin layers are reported in micrograms (μg) for 3 different replicates. A minoxidil mass balance study was also conducted and the % of recovery of minoxidil was better than 95% for both the controls and the inventive formulation.

HPLC Procedure for Minoxidil Quantification

A HPLC System (Waters Alliance® HPLC system) was used to measure minoxidil with UV absorption response at 286 nm. A Luna 5 μM C18(2) 250×4.6-mm HPLC column (Phenomenex) was used to separate the minoxidil analyte from other impurities in the extract samples for surface rinse, stripped tape, epidermis, dermis, and receptor solution. The mobile phase was an isocratic 80% (70:29:1 water/methanol/acetic acid—pH 3.3): 20% methanol.

TABLE 16

|  | Time (hr) | Comparative Treatment Formulation P (microgram) | Comparative Treatment Formulation R (microgram) | Inventive Treatment Formulation Q (microgram) |
|---|---|---|---|---|
| Cumulative Minoxidil in Receptor | 6 | 13.7 | 53.2 | 0.9 |
|  | 24 | 115.0 | 142.2 | 6.5 |
| Dermis | 24 | 24.2 | 15.4 | 73.2 |
| Epidermis | 24 | 118.1 | 119.7 | 163.5 |
| Tape | 24 | 31.5 | 64.7 | 67.3 |

TABLE 17

Minoxidil Skin Penetration Results from tests separately comparing Inventive Treatment Formulation Q vs. Comparative Treatment Formulation R and Comparative Treatment Formulation P vs. Comparative Treatment Formulation R

|  | Time (hr) | Ratio of Comparative Treatment Formulation P to Comparative Treatment Formulation R | Ratio of Inventive Treatment Formulation Q to Comparative Treatment Formulation R | Ratio of Inventive Treatment Formulation Q to Comparative Treatment Formulation P |
|---|---|---|---|---|
| Cumulative Minoxidil in Receptor | 6 | 0.3 | 0.02 | 0.1 |
|  | 24 | 0.8 | 0.05 | 0.1 |
| Dermis | 24 | 1.6 | 4.8 | 3.0 |
| Epidermis | 24 | 0.9 | 1.4 | 1.5 |
| Tape | 24 | 0.5 | 1.0 | 2.1 |

Because the target tissue for topical minoxidil delivery is the hair follicles (or hair "roots") residing deep in the dermis, only minoxidil that penetrated into and cross the dermis layer could reach the hair follicles, and therefore, is of practical significance. The Comparative Treatment Formulation P and Inventive Treatment Formulations Q provided enhanced minoxidil delivery deep into the human skin versus the Comparative Treatment Formulation R (i.e., by about 480% [for Inventive Treatment Formulations Q] and 160% [for Comparative Treatment Formulation P] into the dermis which is where the hair bulb is located), especially in skin tissues, as demonstrated by the results in Table 17. Additionally, Ratio of test results (micrograms) of Inventive Treatment Formulation Q to Comparative Treatment Formulation P (micrograms) demonstrates, by extrapolation, a higher penetration of minoxdil into dermis and epidermis using the $C_8$-$C_{24}$ alcohol ester of a carboxylic acid (i.e. cetyl lactate).

Example 14

A mice hair growth study was performed using the hair growth compositions of the present invention as detailed below.

Procedure:

In vivo hair growth study was conducted in a mouse model similar to that described in Example 3. Five female mice (C3H mice, Charles River Breeding Laboratories, Kingston, N.Y.) were included for each test article.

To determine the acceleration in the onset of the anagen phase in the C3H mice, C3H female mice at 6-7 weeks of age were purchased from Taconic Farms (Germantown, N.Y.). C3H mice's hair growth cycles have similar anagen, catagen and telogen phases. (Miyamoto I.; Hamada K., Journal of Dermatological Science, Volume 10, Number 1, July 1995, pp. 99-99 (1)). The hair growth cycles are shown on Table 18.

TABLE 18

| Weeks after Birth | Hair Growth Stage |
|---|---|
| Week 0 | Morphogenesis |
| Week 2 | Catagen |
| Week 3 | Telogen |
| Week 4 | Anagen |
| Week 6 | Catagen |
| Week 7 | Telogen |
| Week 15 | Anagen |

Each phase is shorter than its corresponding phase in humans and synchronized. This makes C3H mice a useful model for studying the induction activity of hair re-growth by active substances. C3H mice have a long telogen window from week 7 to week 15. Therefore, hair regrowth studies typically start at week 7 and end at week 15, i.e. the duration of a study is about 8 weeks.

Mice were housed in appropriately sized cages in an environmentally controlled room with a 12-hour light-12-hour dark photoperiod and supplied with food and water ad libitum. Animal care was based on the "Guide for the Care and Use of Laboratory Animals", NIH Publication No. 85-23. Once all mice entered their prolonged telogen/resting phase of the hair cycle, they were clipped over the dorsal area about 1.5×5 cm (Wahl Clippers 8900 Series, Blade #1086). Five female mice per group were clipped while sedated with 2% induction and maintenance isoflurane and 0.5 L Oxygen. The actual number of mice represented in the data may vary due to inadvertent death of one or more mice during study.

Determination of Accelerated Onset of Anagen Phase

The mice were shaved with a short hair clipper to hairless on their back as determined by visual inspection (2×5 cm² area) at the start of the study. Test articles were prepared as in the procedures described above. The test articles were applied daily to the shaved areas of the mice daily at 0.2 ml per dose. Both the hair anagen phase and the hair coverage were observed by visual inspection and recorded 5 days a week for each mouse's hair condition (Telogen phase: resting phase in hair growth cycle—shaved skin shown no dark hair bulbs/roots; Anagen phase: anagen follicles, i.e. follicles in the growth state of the hair growth cycle—shaved skin shows dark hair bulbs/roots) A study log (or, Anagen Phase Log) documenting day-to-day observations of mice entering anagen (grey skin, the first visual clue to a new hair growth) were recorded. Treatments continued for 8 weeks.

The treatment groups and treatment formulations were selected as follows:

| Group | Treatment Formulation |
|---|---|
| A | Untreated |
| B | Comparative Treatment Formulation R |
| C | Comparative Treatment Formulation P |
| D | Inventive Treatment Formulation Q |

As shown in Table 19 below, the Inventive Composition Formula Q resulted in hair follicles turning from resting state (telogen phase) to growth state (anagen phase) in about three days faster than the Comparative Treatment Formulation R. The Inventive Composition Formula Q resulted in hair follicles turning from resting state (telogen phase) to growth state (anagen phase) in about four days faster than the Comparative Treatment Formulation R.

TABLE 19

Anagen Phase Onset Log

| Duration after treatment | Untreated | Comparative Treatment Formulation R | Comparative Treatment Formulation P | Inventive Composition Formula Q |
|---|---|---|---|---|
| Day 1 | Telogen | Telogen | Telogen | Telogen |
| Day 2 | Telogen | Telogen | Telogen | Anagen |
| Day 3 | Telogen | Telogen | Anagen | Anagen |
| Day 6 | Telogen | Anagen | Anagen | Anagen |
| Week 2 | Telogen | Anagen | Anagen | Anagen |
| Week 3 | Telogen | Anagen | Anagen | Anagen |
| Week 4 | Telogen | Anagen | Anagen | Anagen |
| Week 5 | Telogen | Anagen | Anagen | Anagen |
| Week 6 | Telogen | Anagen | Anagen | Anagen |

Table 20 shows anagen phase onset times for Untreated, Comparative Treatment Formulation R, Comparative Treatment Formulation P and Inventive Treatment Formulation Q as recorded in the anagen phase log.

TABLE 20

The Anagen Phase Onset

| Group | Treatment Formulation | Anagen Phase Onset (Days after Treatment) |
|---|---|---|
| A | Untreated | 41 |
| B | Comparative Treatment Formulation R | 6 |
| C | Comparative Treatment Formulation P | 3 |
| D | Inventive Treatment Formulation Q | 2 |

The data in Table 20 demonstrates that the onset of anagen phase occurred 3 days earlier in Group C (Comparative Treatment Formulation P) and four days earlier in Group D (Inventive Treatment Formulation Q) than in the Group B (Comparative Treatment Formulation R). Group C is 38 days while Group D is 39 days earlier than in Group A of untreated.

The average degree of terminal hair coverage across mice in each Group was determined by visual inspection of the images taken weekly. A hair coverage index was used in documenting the mice hair growth stages. The phrase "degree of terminal hair coverage", means the observed average estimated percentage of the treated site which is covered by terminal hair.

The phrase "faster degree of terminal hair coverage" means that a degree of terminal hair coverage is achieved faster in time. The term "average" means the average across the mice in each group. The term "observed" or "visual observations" means visual inspection.

The groups were then ranked in order of highest degree of terminal hair coverage to lowest degree of terminal hair coverage according to the following hair coverage scoring system.

Hair Coverage Scoring System

| Grading | Description |
|---|---|
| 0 | No hair at all |
| 1 | A few patches of hair growth, less than ¼ of the dorsal area |
| 2 | Hair growth covering about ¼ of the dorsal area |
| 3 | Hair growth covering about ½ of the dorsal area |
| 4 | Hair growth covering more than ¾ of the dorsal area |
| 5 | Hair growth completely covering treatment area |

Table 21 is a ranking of the degree of terminal hair coverage for Comparative Treatment Formulation P, Comparative Treatment Formulation R, Inventive Treatment Formulation Q and Untreated, based on images taken at different time points. Visual observation of images taken at week 0 (day that mice were shaved) demonstrated that, at this stage of the study, all the mice of test groups had all terminal hair removed.

TABLE 21

Hair Coverage Score Table for Mice Shaved Hair (n = 5 per cell at the study start

|  | Untreated | | Comparative Treatment Formulation R | | Comparative Treatment Formulation P | | Inventive Composition Treatment Formula Q | |
|---|---|---|---|---|---|---|---|---|
|  | Individual | | Individual | | Individual | | Individual | |
| Week | Individual Score | Ave. Score | Score (per mouse) | Ave. Score | Score (per mouse) | Ave. Score | Score (per mouse) | Ave. Score |
| 1 | 0, 0, 0 | 0 | 0, 0, 0, 0, 0 | 0 | 2, 1, 2, 3, 3 | 2 | 1, 1, 1, 1, 1 | 1 |
| 2 | 0, 0, 0 | 0 | 1, 1, 1, 1, 1 | 1 | 0, 1, 1, 1, 2 | 1 | 2, 2, 2, 2, 2 | 2 |
| 3 | 0, 0, 0 | 0 | 1, 1, 1, 1, 1 | 1 | 3, 3, 3, 3 | 3 | 3, 3, 3, 3, 3 | 3 |
| 4 | 0, 0, 0 | 0 | 1, 1, 1, 1, 1 | 1 | 4, 4, 5, 5* | 4.5 | 5, 5, 5, 5, 5 | 5 |
| 5 | 0, 0, | | 1, 1, 1, 1, 1 | 1 | — | — | 5, 5, 5, 5, 5 | 5 |
| 6 | 0, 0, 0 | 0 | 1, 2, 3* | 2 | 5, 5, 5, 5* | 5 | 5, 5, 5, 5, 5 | 5 |
| 7 | 1, 1, 1 | 1 | 1, 4, 4* | 3 | 5, 5, 5, 5** | 5 | 5, 5, 5, 5, 5 | 5 |

*One test mice was sacrificed after Week 4 evaluation for tissue histology

The ranking in Table 6 demonstrates that mice skin treated with Inventive Treatment Formulation Q, containing the non-ionic lipid (steareth-10) and $C_8$-$C_{24}$ alcohol ester of a carboxylic acid (i.e., cetyl lactate), demonstrated a much faster degree of terminal hair coverage than the Comparative Treatment Formulation R containing the non-ionic lipid (steareth-10) and no $C_8$-$C_{24}$ alcohol ester of a carboxylic acid (i.e., cetyl lactate). However, it was surprising that the hair started to fall off from newly growing areas with the treatment of the Comparative Treatment Formulation R. The Inventive Treatment Formulation Q containing the $C_8$-$C_{24}$ alcohol ester of a carboxylic acid (i.e., cetyl lactate) in addition to the the non-ionic lipid (steareth-10) did not show this hair falling off effect and it grew the mice hair the fastest.

Example 15

Compositions incorporating the hair growth composition of the present invention were prepared using conventional mixing technology and Example formula I and II are illustrated in Table 22.

TABLE 22

Comparative Formulation I and Inventive Treatment Formulation II

| Chemical Name | Comparative Formulation I % (w/w) | Inventive Treatment Formulation II % (w/w) |
|---|---|---|
| Ethyl Alcohol | 21.00 | 21.00 |
| Pentylene Glycol | 4.00 | 4.00 |
| Glycerin | 12.00 | 12.00 |
| Citric Acid | 0.20 | 0.20 |
| Lactic Acid | 3.00 | 3.00 |
| Minoxidil | 5.07 | 5.07 |
| Butylated Hydroxytoluene | 0.10 | 0.10 |
| Steareth-10 | 1.50 | 1.50 |
| Cetyl lactate | n/a | 1.50 |
| Water | 50.63 | 49.13 |
| Polyquaternium-37 | 2.50 | 2.50 |
| pH = 4.50 | 100.00 | 100.00 |

Comparative Formulation I and Inventive Treatment Formulation II were prepared according to the following procedure:

(1) The ethyl alcohol is added to a suitably sized first glass container with an overhead mixer.
(2) The pentylene glycol, glycerin, citric acid, & lactic acid are added to the container and the mixture is mixed for about 2 minutes.
(3) The minoxidil, and BHT are added to the beaker and is stirred for about 10 minutes or until dissolved.
(4) The water is added slowly and the mixture is mixed for about 2 minutes.
(5) In a separate second beaker equipped with a hotplate and magnetic stirrer, the steareth-10, and cetyl lactate acetate are premixed.
(6) The premix heated to about 60° C. and is stirred with the magnetic stirring bar until completely melted and a uniform oil phase is formed.
(7) The premix is added with stirring to the minoxidil containing water phase in the first container and is mixed for about 5 minutes.
(9) The Polyquaternium 37 is added to the first container and the mixture in the first container is homogenized at 7,000 rpm using a Silverson L4RT homogenizer (Silverson, Birmingham, UK) for about 5 minutes.

Example 16

In vitro skin permeation of 5% minoxidil compositions through human cadaver skin.

The skin penetration study as described in Example 5 was used to evaluate the penetration of minoxidil into different skin layers for the Inventive Treatment Formulation II vs. Comparative Formulation I.

A cadaver skin sample from a commercial tissue bank (Allosource, Centenia, Colo., dermatomed to approximately 0.4 mm) was cut to fit the glass diffusion cell and mounted skin on the Franz cell. A test sample of 20 microliters was applied on the skin surface. Samples were collected from the receptor compartment at scheduled time points of 0, 2, 4 and 6 hours.

At the end of the study the skin surface was washed with a cotton swab of liquid receptor (PBS). After washing, skin extraction was performed either on full skin or on separated skin layers of epidermis and dermis. Samples collected from the receptor compartment and from the skin extraction were analyzed for minoxidil levels with a Waters High-performance liquid chromatography (HPLC) system with the procedure listed below. The results are shown in Table 23.

The final average minoxidil levels in different skin layers are reported in micrograms (μg) for 3 different replicates. A minoxidil mass balance study was also conducted and the % of recovery of minoxidil was better than 95% for both the control and the inventive formulation.

HPLC Procedure for Minoxidil Quantification

A HPLC System (Waters Alliance® HPLC system) was used to measure minoxidil with UV absorption response at 286 nm. A Luna 5 μM C18(2) 250×4.6-mm HPLC column (Phenomenex) was used to separate the minoxidil analyte from other impurities in the extract samples for surface rinse, stripped tape, skin (epidermis/dermis), and receptor solution. The mobile phase was an isocratic 80% (70:29:1 water/methanol/acetic acid—pH 3.3): 20% methanol.

Formulation I (i.e., by about 206% into the skin tissues) as demonstrated by the results in Table 23.

Example 17

Additional compositions incorporating the composition of the present invention can be prepared using conventional mixing technology (or, as described in Example 1) and are illustrated in Examples j-o of Table 24.

TABLE 24

| Chemical Name | j % (w/w) | K % (w/w) | l % (w/w) | m % (w/w) | n % (w/w) | o % (w/w) |
|---|---|---|---|---|---|---|
| Ethyl Alcohol | 21 | 21 | 53.5 | 30 | 25 | 15 |
| Pentylene glycol | — | — | — | 10 | 3 | — |
| Propylene glycol | 10 | 10 | — | 1 | 1 | 5 |
| Steareth-10 | 1.5 | 1.5 | — | 1 | 1 | — |
| Steareth-2 | 2.0 | 2.0 | — | — | — | — |
| Glyceryl Stearate | — | — | — | 1 | 0.5 | — |
| Glycerin | 10 | 10 | 3 | 10 | 12 | 10 |
| Citric Acid | — | — | 0.2 | 0.1 | 0.1 | 0.1 |
| Lactic Acid | 3.0 | 3.0 | 1.2 | 1 | 2.4 | 3.2 |
| Minoxidil | 5.0 | 5.0 | 5 | 10 | 5 | 3 |
| Butylated Hydroxytoluene | 0.1 | 0.1 | 0.1 | 0.1 | 0.1 | 0.1 |
| Water | 43.83 | 43.83 | 33 | 34.3 | 46.9 | 59.6 |
| Carboxymethylcelluose | 0.75 | 0.50 | — | — | — | — |
| Hydroxyethylcellulose | — | — | 1 | 1 | 1 | 1 |
| Mixture of $C_{12-15}$ Alkyl Lactate[1] | 3.0 | 3.0 | 1.5 | 1.5 | — | — |
| Cetyl Lactate | — | — | 1.5 | — | 3 | 3 |
| Total | 100 | 100 | 100 | 100 | 100 | 100 |
| Viscosity (cps) | 13000 | 8650 | Not measured | Not measured | Not measured | Not measured |
| Physical stability at 4° C. | stable | stable | Not measured | Not measured | Not measured | Not measured |
| Physical stability at 40° C. | stable | stable | Not measured | Not measured | Not measured | Not measured |

[1]Supplied by Ashland (NJ, USA)

Examples j and k of Table 24 show that compositions comprising carboxymethylcelluose and the mixture of $C_{12-15}$ alkyl lactate show physical stability (i.e., no phase separation) at temperatures as low as 4° C. and as high as 40° C. after 1 week of storage at each such temperature as described above.

Example 18

Hair growth compositions of the present invention incorporating select ratios of nonionic hydroxypropylmethyl cellulose (HPMC) to high molecular weight carboxymethyl cellulose (CMC) were prepared using conventional mixing technology. These compositions showed stability after 1 week of storage (at 4° C. and 40° C.) as described above and are detailed as Inventive Treatment Formulations QQ, RR and SS in Table 25.

TABLE 23

| | Time (hr) | Comparative Formulation I (microgram) | Inventive Treatment Formulation II (microgram) | Ratio of Inventive Treatment Formulation II to Comparative Formulation I |
|---|---|---|---|---|
| Cumulative Minoxidil in Receptor | 2 | 58.6 | 56.4 | 0.96 |
| | 4 | 128.8 | 117.1 | 0.91 |
| | 6 | 185.1 | 173.5 | 0.94 |
| Skin | 6 | 67.4 | 138.5 | 2.06 |
| Tapes | 6 | 24.4 | 56.2 | 2.31 |
| % Recovered | | 95.5 | 95.3 | |

Because the target tissue for topical minoxidil delivery is the hair follicles (or hair "roots") residing deep in the dermis, only minoxidil that penetrated into and cross the skin layer could reach the hair follicles, and therefore, is of practical significance. The cetyl lactate (or $C_8$-$C_{24}$ alcohol ester of a carboxylic acid) containing Inventive Treatment Formulation II provided significantly enhanced minoxidil delivery deeper into the human skin versus Comparative

TABLE 25

Inventive Treatment Formulations QQ, RR and SS

| Chemical Name | Inventive Treatment Formulation QQ | Inventive Treatment Formulation RR | Inventive Treatment Formulation SS |
|---|---|---|---|
| Ethyl Alcohol | 21.00 | 21.00 | 21.00 |
| Propylene Glycol | 10.00 | 10.00 | 10.00 |
| Glycerin | 10.00 | 10.00 | 10.00 |
| Citric Acid | 0.20 | 0.20 | 0.20 |

TABLE 25-continued

Inventive Treatment Formulations QQ, RR and SS

| Chemical Name | Inventive Treatment Formulation QQ | Inventive Treatment Formulation RR | Inventive Treatment Formulation SS |
|---|---|---|---|
| Lactic Acid | 3.00 | 3.00 | 3.00 |
| Minoxidil | 5.00 | 5.00 | 5.00 |
| Butylated Hydroxytoluene | 0.10 | 0.10 | 0.10 |
| Water | 44.40 | 44.15 | 43.20 |
| Carboxymethylcellulsoe sodium salt | 0.25 | 0.25 | 0.25 |
| Hydroxypropylmethyl cellulose | 0.75 | 1.00 | 0.75 |
| Steareth-2 | 1.3 | 1.3 | 2.00 |
| Steareth-10 | 1.00 | 1.00 | 1.50 |
| Myristyl Lactate | 3.00 | 3.00 | 3.00 |
| Total | 100 | 100 | 100 |
| Physical stability at 4° C. | stable | stable | stable |
| Physical stability at 40° C. | stable | stable | stable |

Inventive Treatment Formulations QQ, RR and SS were each prepared according to the following procedure:
(1) The ethyl alcohol is added to a suitably sized first glass container with an overhead mixer.
(2) The propylene glycol, glycerin, citric acid, & lactic acid are added to the container and the mixture is mixed for about 2 minutes.
(3) The minoxidil, and BHT are added to the beaker and is stirred for about 10 minutes or until dissolved.
(4) The water is added slowly and the mixture is mixed for about 2 minutes.
(5) In a separate second beaker equipped with a hotplate and magnetic stirrer, the steath, 2, steareth-10, and myristyl lactate acetate are premixed.
(6) The premix heated to about 60° C. and is stirred with the magnetic stirring bar until completely melted and a uniform oil phase is formed.
(7) The premix is added with stirring to the minoxidil containing water phase in the first container and is mixed for about 5 minutes.
(9) The CMC and HPMC are added to the first container and the mixture in the first container is homogenized at 7,000 rpm using a Silverson L4RT homogenizer (Silverson, Birmingham, UK) for about 5 minutes.

Example 19

A mice hair growth study was performed using the hair growth compositions of the present invention Inventive Treatment Formulations QQ, RR and SS vs. a commercially available Walgreen's 5% Minoxidil Topical Solution was used as Comparative Formulation TT. (The pH of the Walgreen's 5% Minoxidil Topical Solution was measured to be 8.1.)
Procedure:
In vivo hair growth study was conducted in a mouse model similar to that described in U.S. Pat. No. 6,419,913 B1, which patent is hereby incorporated by reference. Five female mice (C3H mice, Charles River Breeding Laboratories, Kingston, N.Y.) were included for each test article (i.e., inventive and comparative test formulations of Examples 1 and 2).

To determine the acceleration in the onset of the anagen phase in the C3H mice, C3H female mice at 6-7 weeks of age were purchased from Taconic Farms (Germantown, N.Y.). C3H mice's hair growth cycles have similar anagen, catagen and telogen phases. (Miyamoto I.; Hamada K., Journal of Dermatological Science, Volume 10, Number 1, July 1995, pp. 99-99 (1)). The hair growth cycles are shown on Table 26.

TABLE 26

| Weeks after Birth | Hair Growth Stage |
|---|---|
| Week 0 | Morphogenesis |
| Week 2 | Catagen |
| Week 3 | Telogen |
| Week 4 | Anagen |
| Week 6 | Catagen |
| Week 7 | Telogen |
| Week 15 | Anagen |

Each phase is shorter than its corresponding phase in humans and synchronized. This makes C3H mice a useful model for studying the induction activity of hair re-growth by active substances. C3H mice have a long telogen window from week 7 to week 15. Therefore, hair regrowth studies typically start at week 7 and end at week 15, i.e. the duration of a study is about 8 weeks.

Mice were housed in appropriately sized cages in an environmentally controlled room with a 12-hour light-12-hour dark photoperiod and supplied with food and water ad libitum. Animal care was based on the "Guide for the Care and Use of Laboratory Animals", NIH Publication No. 85-23. Once all mice entered their prolonged telogen/resting phase of the hair cycle, they were clipped over the dorsal area about 1.5×5 cm (Wahl Clippers 8900 Series, Blade #1086). Five female mice per group were clipped while sedated with 2% induction and maintenance isoflurane and 0.5 L Oxygen. The actual number of mice represented in the data may vary due to inadvertent death of one or more mice during study.
Determination of Accelerated Onset of Anagen Phase The mice were shaved with a short hair clipper to hairless on their back as determined by visual inspection (2×5 $cm^2$ area) at the start of the study. Test articles were prepared as described above. The test articles were applied daily to the shaved areas of the mice daily at 0.2 ml per dose. Both the hair anagen phase and the hair coverage were observed by visual inspection and recorded 5 days a week for each mouse's hair condition (Telogen phase: resting phase in hair growth cycle—shaved skin shown no dark hair bulbs/roots; Anagen phase: anagen follicles, i.e. follicles in the growth state of the hair growth cycle—shaved skin shows dark hair bulbs/roots) A study log (or, Anagen Phase Log) documenting day-to-day observations of mice entering anagen (grey skin, the first visual clue to a new hair growth) were recorded. Treatments continued for 8 weeks.

The treatment groups and treatment formulations were selected as follows:

| Group | Treatment Formulation |
|---|---|
| A | Untreated |
| B | Comparative Formulation TT |
| C | Inventive Treatment Formulation QQ |
| D | Inventive Treatment Formulation RR |
| E | Inventive Treatment Formulation SS |

As shown in Table 27 below, the Inventive Treatment Formulations QQ, RR and SS each resulted in hair follicles turning from resting state (telogen phase) to growth state (anagen phase) in about four days faster than the Comparative Treatment Formulation TT.

TABLE 27

Anagen Phase Onset Log

| Duration after treatment | Untreated | Inventive Treatment Formulation QQ (microgram) | Inventive Treatment Formulation RR (microgram) | Inventive Treatment Formulation SS | Comparative Formulation TT |
|---|---|---|---|---|---|
| Day 1 | Telogen | Telogen | Telogen | Telogen | Telogen |
| Day 2 | Telogen | Anagen | Anagen | Anagen | Telogen |
| Day 3 | Telogen | Anagen | Anagen | Anagen | Telogen |
| Day 6 | Telogen | Anagen | Anagen | Anagen | Anagen |
| Week 2 | Telogen | Anagen | Anagen | Anagen | Anagen |
| Week 3 | Telogen | Anagen | Anagen | Anagen | Anagen |
| Week 4 | Telogen | Anagen | Anagen | Anagen | Anagen |
| Week 5 | Telogen | Anagen | Anagen | Anagen | Anagen |
| Week 6 | Telogen | Anagen | Anagen | Anagen | Anagen |

Table 28 shows anagen phase onsets for Untreated, Comparative Treatment Formulation TT and Inventive Treatment Formulations QQ, RR and SS as recorded in the anagen phase log.

TABLE 28

Anagen Phase Onset

| Group | Treatment Formulation | Anagen Phase Onset (Days after Treatment) |
|---|---|---|
| A | Untreated | 42 |
| B | Comparative Formulation TT | 6 |
| C | Inventive Treatment Formulation QQ | 2 |
| D | Inventive Treatment Formulation RR | 2 |
| E | Inventive Treatment Formulation SS | 2 |

The data in Table 28 demonstrates that the onset of anagen phase occurred 4 days earlier in Group C (Test Formula 2) than in the Group B (Test Formula 1). Group C is 40 days earlier than in Group A of untreated.

The average degree of terminal hair coverage across mice in each Group was determined by visual inspection of the images taken weekly. A hair coverage index was used in documenting the mice hair growth stages. The phrase "degree of terminal hair coverage", means the observed average estimated percentage of the treated site which is covered by terminal hair.

The phrase "faster degree of terminal hair coverage" means that a degree of terminal hair coverage is achieved faster in time. The term "average" means the average across the mice in each group. The term "observed" or "visual observations" means visual inspection.

The groups were then ranked in order of highest degree of terminal hair coverage to lowest degree of terminal hair coverage according to the following hair coverage scoring system.

Hair Coverage Scoring System

| Grading | Description |
|---|---|
| 0 | No hair at all |
| 1 | A few patches of hair growth, less than ¼ of the dorsal area |
| 2 | Hair growth covering about ¼ of the dorsal area |
| 3 | Hair growth covering about ½ of the dorsal area |
| 4 | Hair growth covering more than ¾ of the dorsal area |
| 5 | Hair growth completely covering treatment area |

Table 29 is a ranking of the degree of terminal hair coverage for Test Formulation 1, Test formula 2 and Untreated, based on images taken at different time points. Visual observation of images taken at week 0 (day that mice were shaved) demonstrated that, at this stage of the study, all the mice of test groups had all terminal hair removed.

TABLE 29

Hair Coverage Score Table for Mice Shaved Hair (n = 5 per cell at the study start)

| | Untreated Hair Coverage Score | | Comparative Formulation TT Hair Coverage Score | | Inventive Treatment Formulation QQ Hair Coverage Score | | Inventive Treatment Formulation SS Hair Coverage Score | | Inventive Treatment Formulation RR Hair Coverage Score | |
|---|---|---|---|---|---|---|---|---|---|---|
| Week | Per mouse | Ave. | Per mouse | Ave. | Per mouse | Ave. | Per mouse | Ave. | Per mouse | Ave. |
| 1 | 0, 0, 0, 0, 0 | 0 | 0, 0, 0, 0, 0 | 0 | 1, 1, 1, 0.5, 0.5 | 0.8 | 1, 1, 1, 0.5, 0.5 | 0.8 | 0.5, 0.5, 1, 1, 1 | 0.8 |
| 2 | 0, 0, 0, 0, 0 | 0 | 0, 0, 0, 0, 1 | 0.2 | 1, 1, 1.5, 1, 0.5 | 1.0 | 2, 1, 1.5, 1, 0.5 | 1.2 | 1, 1, 1, 1, 1.5 | 1.1 |
| 3 | 0, 0, 0, 0, 0 | 0 | 0, 0, 1, 1, 2 | 0.8 | 2, 3, 4, 4, 4 | 3.4 | 5, 3, 4, 3, 3 | 3.6 | 3, 3, 3, 4, 5 | 3.7 |
| 4 | 0, 0, 0, 0, 0 | 0 | 0, 1, 1, 2, 2 | 1.2 | 5, 5, 5, 5, 5 | 5 | 5, 5, 5, 5, 5 | 5 | 5, 5, 5, 5, 5 | 5 |
| 5 | 0, 0, 0, 0, 0 | 0 | 0.5.1, 2, 2, 4 | 1.9 | 5, 5, 5, 5, 5 | 5 | 5, 5, 5, 5, 5 | 5 | 5, 5, 5, 5, 5 | 5 |
| 6 | 0, 0, 0, 0, 1 | 0.2 | 1, 3, 4, 4, 5 | 3.4 | 5, 5, 5, 5, 5 | 5 | 5, 5, 5, 5, 5 | 5 | 5, 5, 5, 5, 5 | 5 |
| 7 | 0, 0, 0, 0, 1 | 0.2 | 2, 4, 4, 5, 5 | 4 | 5, 5, 5, 5, 5 | 5 | 5, 5, 5, 5, 5 | 5 | 5, 5, 5, 5, 5 | 5 |

The ranking in Table 29 demonstrates that mice skin treated with Inventive Treatment Formulations QQ, RR, and SS containing myristal lactate demonstrated a much faster degree of terminal hair coverage than the Comparative Formulation TT.

Example 20

Formulation examples p-v are compositions incorporating the composition of the present invention. The compositions of examples p-v comprise select ratios of nonionic hydroxypropylmethyl cellulose (HPMC) to high molecular weight carboxymethyl cellulose (CMC) and can be prepared using conventional mixing technology (or, as described in Example 18) and are illustrated in Table 30 and showing stability assessment after 1 week of storage (at 4° C. and 40° C.) as described above under definition of storage stability.

TABLE 30

Assessment of Temperature Stability after 1 Week of Storage

| Chemical Name | p % (w/w) | q % (w/w) | r % (w/w) | s % (w/w) | t % (w/w) | u % (w/w) | v % (w/w) |
|---|---|---|---|---|---|---|---|
| Ethyl Alcohol | 21.00 | 21.00 | 21.00 | 21.00 | 21.00 | 21.00 | 21.00 |
| Propylene Glycol | 10.00 | 10.00 | 10.00 | 10.00 | 10.00 | 10.00 | 10.00 |
| Glycerin | 10.00 | 10.00 | 10.00 | 10.00 | 10.00 | 10.00 | 10.00 |
| Citric Acid | 0.20 | 0.20 | 0.20 | 0.20 | 0.20 | 0.20 | 0.20 |
| Lactic Acid | 3.00 | 3.00 | 3.00 | 3.00 | 3.00 | 3.00 | 3.00 |
| Minoxidil | 5.00 | 5.00 | 5.00 | 5.00 | 5.00 | 5.00 | 5.00 |
| Butylated Hydroxytoluene | 0.10 | 0.10 | 0.10 | 0.10 | 0.10 | 0.10 | 0.10 |
| Water | 44.40 | 44.40 | 44.40 | 44.40 | 44.40 | 44.40 | 43.90 |
| Carboxymethylcellulose sodium salt (CMC)[1] | 0.25 | 0.33 | 0.50 | 0.67 | 1.00 | 0.00 | 0.75 |
| Hydroxypropylmethyl cellulose (HPMC)[2] | 0.75 | 0.67 | 0.50 | 0.33 | 0.00 | 1.00 | 0.75 |
| Steareth-2 | 1.30 | 1.30 | 1.30 | 1.30 | 1.30 | 1.30 | 1.30 |
| Steareth-10 | 1.00 | 1.00 | 1.00 | 1.00 | 1.00 | 1.00 | 1.00 |
| Myristyl Lactate | 3.00 | 3.00 | 3.00 | 3.00 | 3.00 | 3.00 | 3.00 |
| Total | 100 | 100 | 100 | 100 | 100 | 100 | 100 |
| Physical stability at 4° C. | stable | stable | stable | unstable | unstable | stable | stable |
| Physical stability at 40° C. | stable | stable | stable | stable | stable | unstable | stable |
| Ratio of HPMC vs. CMC | 3:1 | 2:1 | 1:1 | 1:2 | 0:1 | 1:0 | 1:1 |
| Viscosity* | 3433 cps | 5933 cps | 7266 cps | 12100 cps | 23800 cps | 1050 cps | 17000 cps |
| Total concentration of | 1.00 | 1.00 | 1.00 | 1.00 | 1.00 | 1.00 | 1.50 |

*Measured using a Brookfield RV (spindle 4, speed 6 RPM at 1 minute following the temperature equilibration at 25° C. ± 1° C.)
[1]Aqualon CMC 7HF PH, Ashland, Wilmington, DE, USA
[2]Methocel E 10M, Dow Chemical, Miland, MC, USA Table 30 shows that examples p through r and v, having ratios of HPMC to CMC of 3:1, 2:1 and 1:1, respectively, provide compositions which are physically stable (i.e., no phase separation) at temperatures as low as 4° C. and as high as 40° C. after 1 week of storage at each such temperature as described above. Table 30 further demonstrates that ratios of HPMC to CMC below 1:1 or greater than 10:1, as in examples s-u (ratios of HPMC to CMC of 1:2, 0:1 and 1:0, respectively), fail to provide the physical stability at both 4° C. and 40° C. after 1 week of storage.

Example 21

The stability of the compositions of formulation examples p-v of Example 20 were reassessed after 7 weeks of storage. The formulations of examples p-v of Example 20 are reproduced in Table 31, including stability assessment after 7 weeks of storage (at 4° C. and 40° C.) as described above under definition of storage stability.

TABLE 31

Assessment of Temperature Stability after 7 Weeks of Storage

| Chemical Name | p % (w/w) | q % (w/w) | r % (w/w) | s % (w/w) | t % (w/w) | u % (w/w) | v % (w/w) |
|---|---|---|---|---|---|---|---|
| Ethyl Alcohol | 21.00 | 21.00 | 21.00 | 21.00 | 21.00 | 21.00 | 21.00 |
| Propylene Glycol | 10.00 | 10.00 | 10.00 | 10.00 | 10.00 | 10.00 | 10.00 |
| Glycerin | 10.00 | 10.00 | 10.00 | 10.00 | 10.00 | 10.00 | 10.00 |
| Citric Acid | 0.20 | 0.20 | 0.20 | 0.20 | 0.20 | 0.20 | 0.20 |
| Lactic Acid | 3.00 | 3.00 | 3.00 | 3.00 | 3.00 | 3.00 | 3.00 |
| Minoxidil | 5.00 | 5.00 | 5.00 | 5.00 | 5.00 | 5.00 | 5.00 |
| Butylated Hydroxytoluene | 0.10 | 0.10 | 0.10 | 0.10 | 0.10 | 0.10 | 0.10 |
| Water | 44.40 | 44.40 | 44.40 | 44.40 | 44.40 | 44.40 | 43.90 |
| Carboxymethylcellulose sodium salt (CMC)[1] | 0.25 | 0.33 | 0.50 | 0.67 | 1.00 | 0.00 | 0.75 |
| Hydroxypropylmethyl cellulose (HPMC)[2] | 0.75 | 0.67 | 0.50 | 0.33 | 0.00 | 1.00 | 0.75 |
| Steareth-2 | 1.30 | 1.30 | 1.30 | 1.30 | 1.30 | 1.30 | 1.30 |
| Steareth-10 | 1.00 | 1.00 | 1.00 | 1.00 | 1.00 | 1.00 | 1.00 |
| Myristyl Lactate | 3.00 | 3.00 | 3.00 | 3.00 | 3.00 | 3.00 | 3.00 |
| Total | 100 | 100 | 100 | 100 | 100 | 100 | 100 |
| Physical stability at 4° C. | stable | unstable | unstable | unstable | unstable | stable | unstable |
| Physical stability at 40° C. | stable | stable | stable | stable | stable | unstable | stable |
| Ratio of HPMC vs. CMC | 3:1 | 2:1 | 1:1 | 1:2 | 0:1 | 1:0 | 1:1 |
| Viscosity* | 3433 cps | 5933 cps | 7266 cps | 12100 cps | 23800 cps | 1050 cps | 17000 cps |
| Total concentration of | 1.00 | 1.00 | 1.00 | 1.00 | 1.00 | 1.00 | 1.50 |

*Measured using a Brookfield RV (spindle4, speed 6 RPM at 1 minute following the temperature equilibration at 25° C. ± 1° C.)
[1]Aqualon CMC 7HF PH, Ashland, Wilmington, DE, USA
[2]Methocel E 10M, Dow Chemical, Miland, MC, USA Table 31 shows that example p, having a ratio of HPMC to CMC of 3:1, provides compositions which are physically stable (i.e., no phase separation) at temperatures as low as 4° C. and as high as 40° C. after 7 weeks of storage at each such temperature as described above. Table 31 further demonstrates that ratios of HPMC to CMC below 3:1 or greater than 10:1 (as in examples q-v) fail to provide stability at both 4° C. and 40° C. after 7 weeks.

Example 22

Formulation examples i-ix of Example 22 are compositions incorporating the composition of the present invention. These examples i-ix comprise monohydric alcohols and dihydric alcohols at a total of concentration greater than 36% (w/w) of the total composition (due to the higher alkyl lactate concentrations [i.e., greater 1% by weight of total composititon]) and can be prepared using conventional mixing technology (or, as described in Example 1). These examples i-ix are detailed in Table 32 and 33.

TABLE 32

| Chemical Name | i % (w/w) | ii % (w/w) | iii % (w/w) | iv % (w/w) | v % (w/w) |
|---|---|---|---|---|---|
| Ethyl Alcohol | 30.0 | 30.0 | 30.0 | 30.0 | 30.0 |
| Propylene glycol | 20.0 | 20.0 | 20.0 | 10.0 | 0.0 |
| Glycerin | 5.0 | 5.0 | — | 10.0 | 20.0 |
| Citric Acid | — | — | 0.11 | 0.11 | 0.11 |
| Lactic Acid | 3.0 | 3.0 | 3.0 | 3.0 | 3.0 |
| Minoxidil | 5.0 | 5.0 | 5.00 | 5.0 | 5.0 |
| Butylated Hydroxytoluene | 0.1 | 0.1 | 0.10 | 0.1 | 0.1 |
| Water | 32.65 | 32.45 | 37.29 | 37.29 | 37.29 |
| Hypromellose | 0.75 | 0.75 | 1.00 | 1.00 | 1.00 |

TABLE 32-continued

| Chemical Name | i % (w/w) | ii % (w/w) | iii % (w/w) | iv % (w/w) | v % (w/w) |
|---|---|---|---|---|---|
| Steareth-10 | 0.5 | 0.5 | 0.5 | 0.5 | 0.5 |
| Mixture of $C_{12-15}$ Alkyl Lactate[1] | 3.0 | 3.0 | — | — | — |
| Myristyl Lactate | — | — | 3.0 | 3.0 | 3.0 |
| Allantoin | — | 0.2 | — | — | — |
| Total | 100 | 100 | 100 | 100 | 100 |
| Physical stability at 4° C. | Stable Clear | Stable Clear | Stable | Stable | Slightly Hazy; Stable |
| Physical stability at room temperature 25° C. | Stable | Stable | Stable | Stable | Slightly Hazy; Stable |
| Physical stability at 40° C. | Stable Clear | Stable Clear | Stable Clear | Stable Clear | Physical Separation |
| Viscosity (cps) | 980 | 880 | 1980 | 1680 | 1320 |
| Turbidity (NTU) | 0.906 | 1.04 | 1.54 | 1.13 | 7.8 |
| Relative Dielectric Constant Index | 0.215 | 0.217 | 0.167 | 0.178 | 0.194 |

[1]Supplied by Ashland (NJ, USA)

TABLE 33

| Chemical Name | vi % (w/w) | vii % (w/w) | viii % (w/w) | ix % (w/w) |
|---|---|---|---|---|
| Ethyl Alcohol | 21 | 26 | 21 | 30 |
| Propylene glycol | 20.0 | 20.0 | 15.0 | 10.0 |
| Glycerin | — | — | 5.0 | 10.0 |
| Citric Acid | 0.11 | 0.11 | 0.2 | — |
| Lactic Acid | 3.0 | 3.0 | 3.0 | 3.0 |
| Minoxidil | 5.0 | 5.0 | 5.0 | 5.0 |

TABLE 33-continued

| Chemical Name | vi % (w/w) | vii % (w/w) | viii % (w/w) | ix % (w/w) |
|---|---|---|---|---|
| Butylated Hydroxytoluene | 0.1 | 0.1 | 0.1 | 0.1 |
| Water | 46.29 | 41.04 | 45.2 | 37.4 |
| Hypromellose | 1.0 | 1.0 | 1.0 | 1.0 |
| Steareth-10 | 0.5 | 0.75 | 1.5 | 0.5 |
| Myristyl Lactate | 3.0 | 3.0 | 3.0 | 3.0 |
| Total | 100 | 100 | 100 | 100 |
| Physical stability at 4° C. | Stable | Stable | Stable | Stable |
| Physical stability at 25° C. in 6 months | Hazy | Hazy | Hazy, Clear | Stable Clear |
| Physical stability at 40° C. | Stable Hazy | Stable-Hazy | Physical Separation | Stable Clear |
| Viscosity (cps) | 1020 | 1340 | 880 | 1680 |
| Turbidity (NTU) | 66.5 | 35.2 | 41.5 | 1.13 |
| Relative Dielectric Constant Index (RI) | 0.112 | 0.138 | 0.118 | 0.178 |

Table 32 shows that examples i-iv are "clear" and "stable". Table 32 further shows that examples i-iv have turbidities of less than 6 NTU. For Example v, Table 32 shows mixed results—i.e., for a turbidity greater than 6, we have slight haziness and stability at 4° C. and 25° C., physical separation at 40° C. Table 33 show that examples vi-viii are not stable and hazy where, in each case, the turbidity is above 10 NTU. Example ix was stable and clear with a turbidity lower than 6 NTU. Table 33 further shows that the composition having an RI (as defined above) of greater than 0.15 (i.e., Example ix [RI=0.178], in contrast to Examples vi-viii [RI equal to 0.112, 0.138, and 0.118, respectively]) is observed to be a "clear" composition.

What is claimed is:

1. A composition comprising:
   a. liquid vesicles comprising:
      i. one or more of a hair growth or hair regrowth compound represented by formulas I or II:

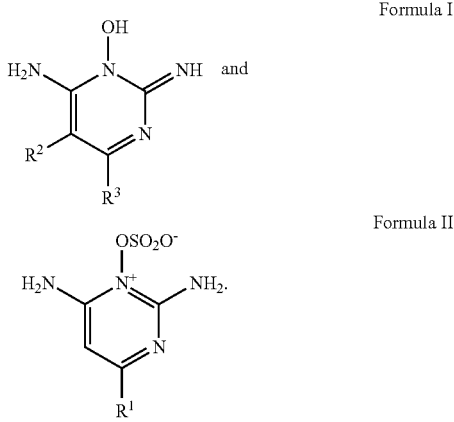

Formula I

Formula II and mixtures thereof, wherein $R^1$ is hydrogen or $-N(R^3)(R^4)$, each $R^3$ and $R^4$ individually is selected from the group consisting of hydrogen, lower alkyl, lower alkenyl, lower aralkyl, and lower cycloalkyl, and taken together $R^3$ and $R^4$ may be a heterocyclic moiety selected from the group consisting of aziridinyl, azetidinyl, pyrrolidinyl, piperidino, hexahydroazepinyl, heptamethylenimino, octamethylenimino, morpholino, and 4-lower-alkylpiperazinyl, each of said heterocyclic moieties having attached as substituents on the carbon atoms 0 to 3 lower alkyl groups, hydroxy or alkoxy, and wherein $R^2$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloaralkyl; tautomers thereof and pharmacologically acceptable acid addition salts thereof; and
      ii. an oil phase consisting of a mixture of $C_{12}$-$C_{15}$ alkyl lactates and, optionally, a long chain fatty acid;
   b. a viscosity modifying agent comprising at least one cellulose or derivative thereof; and
   c. a pharmaceutically acceptable liquid carrier comprising, one or more solubilizer(s), one or more solubilizing acid(s) or mixtures thereof;
   wherein the hair growth or hair regrowth compound is minoxidil, which minoxidil is completely dissolved in the one or more solubilizer(s), one or more solubilizing acid(s) or mixtures thereof and further wherein the liquid vesicles are suspended within the pharmaceutically acceptable liquid carrier and still further wherein the mixture of $C_{12}$-$C_{15}$ alkyl lactates is present at a concentration of about 1.5% to about 3%, by weight of the total composition.

2. The composition of claim 1, wherein the solubilizer comprises one or more $C_1$-$C_3$ alcohol(s), one or more polyhydric alcohol(s) or mixtures thereof.

3. The composition of claim 1, wherein the composition comprises from about 0.1% to about 15% of the minoxidil or a pharmaceutically acceptable salt thereof by weight as the compound of formula I.

4. The composition of claim 3, wherein the composition comprises from about 0.5% to about 10% of the minoxidil or a pharmaceutically acceptable salt thereof by weight.

5. The composition of claim 1, wherein the pharmaceutically acceptable carrier comprises minoxidil or a pharmaceutically acceptable salt thereof.

6. The composition of claim 1 wherein the composition further comprises a polyoxyethylene $C_4$-$C_{26}$ fatty ether.

7. The composition of claim 1 wherein the composition further comprises a polyoxyethylene $C_{10}$-$C_{18}$ fatty ether.

8. The composition of claim 7, wherein the composition comprises from about 0.1% to about 15%, by weight, of the polyoxyethylene $C_4$-$C_{26}$ fatty ether.

9. The composition of claim 1 wherein the cellulose is selected from methyl cellulose; hydroxylalkyl cellulose polymers, alkyl hydroxylalkyl cellulose polymers; or mixtures thereof.

10. The composition of claim 9 wherein the methyl cellulose is selected from methyl cellulose, carboxymethyl cellulose, or mixtures thereof.

11. The composition of claim 9 wherein the composition has a viscosity of from about 50 cps to about 30000 cps as measure by Brookfield RV at spindle 4, speed 6 RPM.

12. The composition of claim 11 wherein the composition has a viscosity of from about 100 cps to about 10000 cps as measure by Brookfield RV at spindle 4, speed 6 RPM.

13. The composition of claim 9 wherein the composition has a yield stress value of from about 0.01 Pa·s to about 5 Pa·s as measured using a TA Instruments ARES G2 Rheometer in accordance with the method described in the specification hereof.

14. The composition of claim 9 wherein the composition has a shear thinning index of 10 or more.

15. The composition of claim 1 wherein the composition comprises from about 0.1% to about 40% by weight of the one of more $C_1$-$C_3$ alcohols.

16. The composition of claim 15 wherein the one or more $C_1$-$C_3$ alcohols comprises ethanol.

17. The composition of claim 1 wherein the liquid vesicle is a non-phospholipid liquid vesicle.

18. The composition of claim 1 wherein the composition is storage stable.

* * * * *